US010624671B2

United States Patent
Swayze et al.

(10) Patent No.: US 10,624,671 B2
(45) Date of Patent: Apr. 21, 2020

(54) TROCAR ATTACHMENT DEVICES AND METHODS

(71) Applicant: Ethicon LLC, Guaynabo, PR (US)

(72) Inventors: Jeffrey S. Swayze, Hamilton, OH (US); Jeffery Kirk, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 564 days.

(21) Appl. No.: 15/387,258

(22) Filed: Dec. 21, 2016

(65) Prior Publication Data
US 2018/0168746 A1  Jun. 21, 2018

(51) Int. Cl.
*A61B 17/34* (2006.01)
*A61B 34/30* (2016.01)
*A61B 17/02* (2006.01)
*A61B 90/50* (2016.01)

(52) U.S. Cl.
CPC ...... *A61B 17/3421* (2013.01); *A61B 17/0218* (2013.01); *A61B 17/3423* (2013.01); *A61B 34/30* (2016.02); *A61B 90/50* (2016.02)

(58) Field of Classification Search
CPC . A61B 17/0218; A61B 17/34; A61B 17/3417; A61B 17/3421; A61B 17/3423; A61B 2017/3425; A61B 2017/3427; A61B 34/30; A61B 2034/302
See application file for complete search history.

(56) References Cited

U.S. PATENT DOCUMENTS

| | | | | |
|---|---|---|---|---|
| 6,478,028 B1* | 11/2002 | Paolitto | ............ | A61B 17/00234 128/898 |
| 8,114,345 B2 | 2/2012 | Dlugos, Jr. et al. | | |
| 8,746,252 B2* | 6/2014 | McGrogan | ......... | A61B 17/3423 128/852 |
| 8,784,435 B2* | 7/2014 | Cooper | .............. | A61B 17/3423 606/130 |
| 8,852,208 B2* | 10/2014 | Gomez | .............. | A61B 17/3423 606/130 |

(Continued)

FOREIGN PATENT DOCUMENTS

WO     2014151621 A1    9/2014
WO  WO-2015142814 A1    9/2015

OTHER PUBLICATIONS

International Search Report and Written Opinion for International App. No. PCT/IB2017/057704 dated Mar. 23, 2018 (14 pages).

*Primary Examiner* — Eric S Gibson
(74) *Attorney, Agent, or Firm* — Mintz Levin Cohn Ferris Glovsky and Popeo, P.C.

(57) ABSTRACT

Methods and devices are provided for attaching a trocar to a surgical arm. For example, a surgical system is provided that has a trocar with a housing and a cannula extending distally from the housing. The housing and the cannula have a tool pathway extending therethrough for receiving a tool. The system also has a trocar support that is configured to be mounted on a distal end of a surgical robotic arm. The trocar is configured to couple to the trocar support through a variety of engagements, such as engaging the trocar in a first configuration that allows free movement of the trocar relative to the trocar support and in a second configuration in which the trocar is locked in a fixed position relative to the trocar support.

17 Claims, 19 Drawing Sheets

(56) References Cited

U.S. PATENT DOCUMENTS

| | | | |
|---|---|---|---|
| 8,945,148 B2* | 2/2015 | Solomon | A61B 17/3423 606/130 |
| 9,096,033 B2* | 8/2015 | Holop | A61B 17/3423 |
| 9,301,807 B2* | 4/2016 | Duval | A61B 17/3423 |
| 9,757,149 B2* | 9/2017 | Cooper | A61B 17/3423 |
| 9,801,654 B2* | 10/2017 | Gomez | A61B 17/3423 |
| 9,955,996 B2* | 5/2018 | Solomon | A61B 17/3423 |
| 10,004,563 B2* | 6/2018 | Gombert | B25J 15/0206 |
| 10,231,791 B2* | 3/2019 | LeBoeuf, II | A61B 5/064 |
| 10,238,422 B2* | 3/2019 | Beckman | A61B 34/30 |
| 2005/0059960 A1* | 3/2005 | Simaan | A61B 34/70 606/1 |
| 2006/0161136 A1 | 7/2006 | Anderson et al. | |
| 2007/0137371 A1* | 6/2007 | Devengenzo | B25J 15/04 74/490.01 |
| 2009/0248040 A1* | 10/2009 | Cooper | A61B 90/10 606/130 |
| 2011/0071543 A1* | 3/2011 | Prisco | A61B 17/0218 606/130 |
| 2011/0071544 A1* | 3/2011 | Steger | A61M 25/0105 606/130 |
| 2011/0178477 A1* | 7/2011 | Morel | A61B 17/3403 604/264 |
| 2011/0277775 A1* | 11/2011 | Holop | A61B 17/3423 128/849 |
| 2011/0277776 A1* | 11/2011 | McGrogan | A61B 17/3423 128/852 |
| 2011/0282351 A1* | 11/2011 | Cooper | A61B 17/3423 606/108 |
| 2011/0282356 A1* | 11/2011 | Solomon | A61B 17/3423 606/130 |
| 2011/0282357 A1* | 11/2011 | Rogers | A61B 17/3423 606/130 |
| 2011/0282358 A1* | 11/2011 | Gomez | A61B 17/3423 606/130 |
| 2011/0282359 A1* | 11/2011 | Duval | A61B 17/3423 606/130 |
| 2013/0079794 A9* | 3/2013 | Cooper | A61B 17/3423 606/108 |
| 2014/0296872 A1* | 10/2014 | Cooper | A61B 17/3423 606/130 |
| 2014/0326254 A1* | 11/2014 | McGrogan | A61B 17/3423 128/849 |
| 2015/0164597 A1* | 6/2015 | McGrogan | A61B 17/3423 606/130 |
| 2015/0305815 A1* | 10/2015 | Holop | A61B 17/3423 128/852 |
| 2015/0374445 A1* | 12/2015 | Gombert | B25J 15/0206 606/130 |
| 2016/0058512 A1* | 3/2016 | Gomez | A61B 17/3423 606/130 |
| 2017/0071628 A1* | 3/2017 | Cooper | A61B 17/3423 |
| 2017/0245888 A1* | 8/2017 | Buyda | A61B 17/00234 |
| 2018/0014852 A1* | 1/2018 | Gomez | A61B 17/3423 |
| 2018/0049824 A1* | 2/2018 | Harris | A61B 34/30 |
| 2018/0168689 A1* | 6/2018 | Beckman | A61B 34/30 |
| 2018/0168746 A1* | 6/2018 | Swayze | A61B 17/3421 |
| 2018/0214176 A1* | 8/2018 | Solomon | A61B 17/3423 |
| 2018/0214224 A1* | 8/2018 | Swayze | A61B 34/37 |
| 2018/0353204 A1* | 12/2018 | Solomon | A61B 17/3423 |
| 2019/0053824 A1* | 2/2019 | Scheib | A61B 34/70 |
| 2019/0231450 A1* | 8/2019 | Waterbury | A61B 34/30 |
| 2019/0254704 A1* | 8/2019 | Buyda | A61B 17/3423 |

* cited by examiner

TROCAR ATTACHMENT DEVICES AND METHODS

FIELD

Methods and devices are provided for attaching a trocar to a surgical arm.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

Various surgical tools and methods are provided for mating a trocar to a surgical robotic arm.

In one embodiment, a surgical system is provided that includes a trocar with a housing and a cannula extending distally from the housing. The housing and the cannula define a tool pathway extending therethrough for receiving a tool. The surgical system also has a trocar support that is configured to be mounted on a distal end of a surgical robotic arm. The trocar support is configured to engage the trocar in a first configuration that allows free movement of the trocar relative to the trocar support. The trocar support is also configured to engage the trocar in a second configuration in which the trocar is locked in a fixed position relative to the trocar support.

The system can vary in a number of ways. For example, the trocar support can include a latch configured to move the trocar support between the first and the second configurations. The latch can be slidable to move the trocar support between the first configuration and the second configuration. The latch can also pivot to move the trocar support between the first configuration and the second configuration. In another example, the latch can be biased to one of the first and second configurations. The trocar support can be configured to automatically engage the trocar in the first configuration when the trocar is mounted onto the trocar support. The trocar support can also include a receiver having a shape that corresponds to a protrusion formed on the trocar for mating the trocar to the trocar support. In another example, the trocar can be freely rotatable relative to the support in the first configuration. In other embodiments, the trocar support can include a linkage assembly for mating the trocar to the trocar support in at least one of the first and second configurations. The trocar support in the first configuration can be configured to prevent axial movement of the trocar along a longitudinal axis of the trocar. The system can also include a robotic arm having the trocar support mated thereto.

In another embodiment, a surgical system can include a trocar with a housing and a cannula extending distally from the housing. The housing and the cannula define a tool pathway extending therethrough for receiving a tool, and the trocar has a mating element formed thereon. The system also has a trocar support that is configured to be mounted on a distal end of a surgical robotic arm and that has at least one receiving feature thereon. The trocar is configured to freely rotatably mate to the trocar support when the mating element is seated within the receiving feature of the trocar support. The trocar support also has a lock configured to engage and prevent movement of the trocar relative to the trocar support.

The system can have numerous variations. For example, the mating element and the receiving feature can include corresponding double dove tail pieces. The trocar can be configured to be locked relative to the trocar support by pivoting the trocar relative to the trocar support. In another example, the system can include alignment features on the trocar and the trocar support for aligning the trocar relative to the trocar support. The receiving feature can be selected from the group consisting of a set of jaws, a sliding block, a hook, and a clamp.

In another aspect, a surgical system is provided that includes a trocar with a housing and a cannula extending distally from the housing. The housing and the cannula have a tool pathway extending therethrough for receiving a tool, and the trocar has a mating element formed thereon. A trocar support is configured to be mounted on a distal end of a surgical robotic arm and has at least one receiving feature thereon. The trocar is configured to mate to the trocar support such that the receiving feature of the trocar support engages and prevents movement of the trocar relative to the trocar support, and the receiving feature is configured to release the trocar through a one-touch release mechanism.

In another aspect, a surgical method is provided that includes inserting a mating feature on a trocar into a receiving feature on a trocar support. The trocar has a housing and a cannula extending distally from the housing. The housing and the cannula define a tool pathway extending therethrough for receiving a tool. The trocar is also freely rotatable but not axially translatable relative to the trocar support. The method can also include activating a locking element on the trocar support to prevent movement of the trocar relative to the trocar support.

BRIEF DESCRIPTION OF THE DRAWINGS

The invention will be more fully understood from the following detailed description taken in conjunction with the accompanying drawings, in which.

DETAILED DESCRIPTION

Figure 1A:
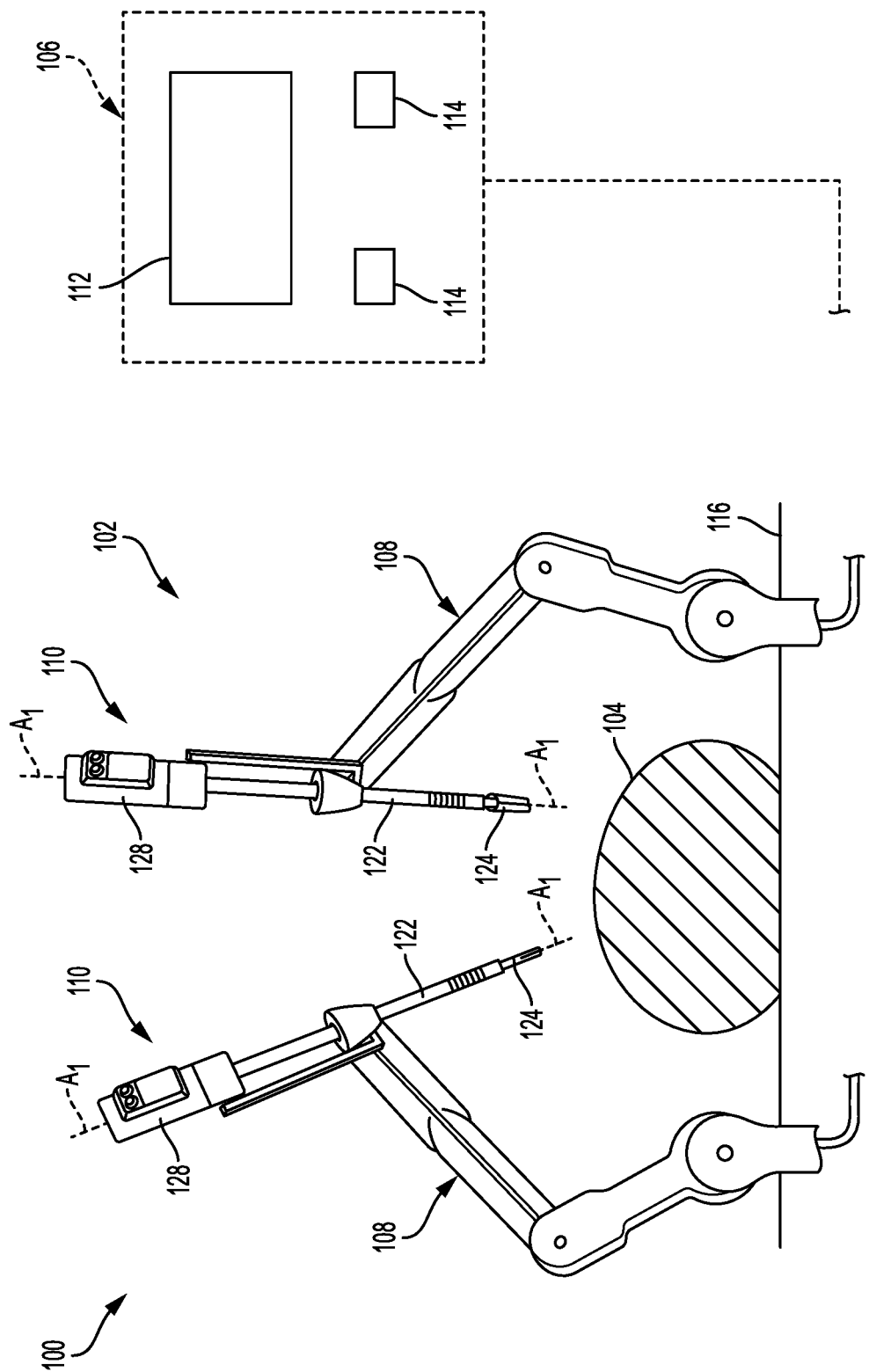
FIG. 1A is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Additionally, WIPO Patent Publication No. WO2014/151621, filed on Mar. 13, 2014 and entitled "Hyperdexterous Surgical System," is incorporated herein by reference.

Various methods and devices are provided for attaching a trocar to a surgical arm. In robotic surgery, a trocar is mounted to a trocar holder on the distal end of a surgical robotic arm, and the trocar provides a pathway through tissue for a surgical tool coupled to the carrier. In general, the trocar can have a housing and a cannula extending from the housing. The housing and the cannula define the tool pathway therethrough.

In many trocars, the insufflation port has a high profile and takes up a lot of space during minimally-invasive surgery. As a result, the insufflation port can interfere with positioning of the trocar, e.g. by hitting the skin surface and/or by hitting other tools and/or other surgical robotic arms. Accordingly, the insufflation port may need to be positioned at a specific location, adjacent to the support, when the trocar is mounted to the support. Connecting a trocar to a trocar support can be challenging, especially when trying to attach the trocar in a quick and timely manner. Additionally, different degrees of attachment may be desired by users. For example, a user may want to connect a trocar to a trocar support while still being able to maneuver, rotate, pivot, reposition, etc. the trocar with respect to the trocar support (for example, while arranging or preparing surgical tools that will be accompanied by insufflation with insufflation tubing that needs to be positioned at the surgical site). At other times, the user may want to connect the trocar to the trocar support such that no relative movement between the trocar and the trocar support is possible (for example, when performing a surgery in which precise movement of a surgical tool is required). Trocars are provided that can quickly and easily couple to a trocar support such that the trocar support allows free movement of the trocar relative to the trocar support. The trocars can also be locked in a fixed position relative to the trocar support.

FIG. 1A is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure.

The patient-side portion 102 can have a variety of configurations. As illustrated in FIG. 1A, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1A). Alternatively, the patient-side portion 102 can include a single assembly that includes one or more robotic arms 108 extending therefrom.

The surgical tool 110 includes an elongate shaft 122, an end effector 124, and a tool housing 128 coupled to a proximal end of the shaft 122. The shaft 122 can have any of a variety of configurations. In general, the shaft 122 is an elongate member extending distally from the housing 128. The shaft 122 is fixed to the housing 128, but in other embodiment the shaft 122 can be releasably coupled to the housing 128 such that the shaft 122 can be interchangeable with other shafts. This may allow a single housing 128 to be adaptable to various shafts having different end effectors. The end effector 124 can also have a variety of sizes, shapes, and configurations. The end effector 124 can be configured to move relative to the shaft 122, e.g., by rotating and/or articulating, to position the end effector 124 at a desired location relative to a surgical site during use of the tool 110.

The housing 128 includes various components (e.g., gears and/or actuators) configured to control the operation various features associated with the end effector 124 (e.g., any one or more of clamping, firing, rotation, articulation, energy delivery, etc.). In at least some embodiments, as in this illustrated embodiment, the tool housing 128 includes coupling features that are configured to allow the releasable coupling of the tool 110 to a tool driver on the robotic arm 108. The tool driver can include motors and actuators for driving the surgical tool. A person skilled in the art will appreciate that the surgical tool 110 can have any of a variety of configurations, and it can be configured to perform at least one surgical function. The surgical tool can be, for example, a stapler, a clip applier, forceps, a grasper, a needle driver, scissors, an electrocautery tool that applies energy, a suction tool, an irrigation tool, an imaging device (e.g., an endoscope or ultrasonic probe), etc.

The control system 114 can also have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and surgical tools 110.

Figure 1B:
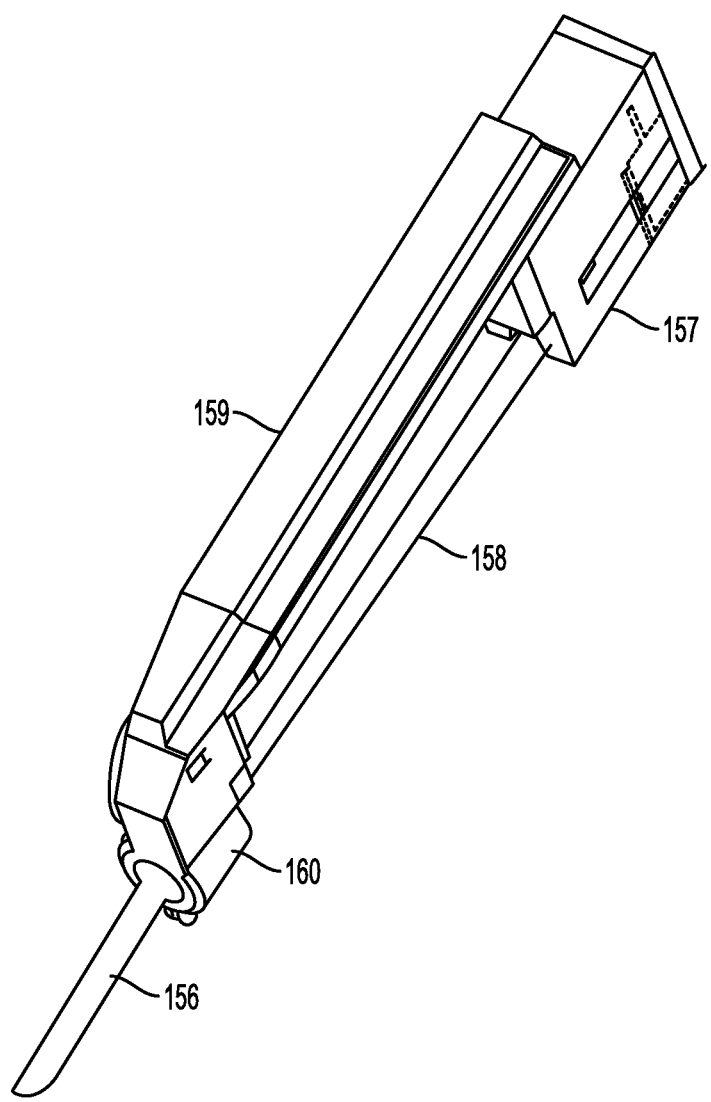
FIG. 1B is a perspective view of one embodiment of a trocar and a tool driver with a tool extending therethrough.

FIG. 1B illustrates another embodiment of a trocar 156 and a tool driver 157 with a surgical tool 158 extending therethrough. The trocar 156 is configured to couple to a surgical robotic arm at a distal end thereof, and the surgical robotic arm can be used with the aforementioned surgical system. The arm can have a configuration similar to that discussed above. The surgical tool 158 can be similar to the surgical tool 110 and be passed through the trocar 156 and into a tissue surface. A carrier 159 can be coupled to the distal end of the robotic arm, and it can include a trocar holder 160 on the distal end thereof and the tool driver 157 on a proximal end thereof. The tool driver 157 can include a plurality of motors, and it can be configured to couple to a housing on the surgical tool 158 such that the motors can drive the various functions of the surgical tool.

As indicated above, surgical tools, such as the surgical tools 110, 158, can extend through a trocar, which can provide support, positioning assistance, insufflation, etc. during use of the surgical tool(s). In robotic surgery, one or more trocars can be mounted on a trocar support on the distal end of one of more robotic arms. In an exemplary embodiment, the trocar support has two mating configurations. In a first configuration, the trocar support engages the trocar yet allows free movement of the trocar, such as rotation of the trocar. In a second mating configuration, the trocar support locks the trocar in a fixed position to prevent movement thereof.

FIGS. 2A-2G illustrate one embodiment of a trocar 200 with a housing 202 and a cannula 204, and a trocar support 220 for mating to the trocar 200. As shown, the trocar 200 generally includes a housing 202 having a cannula 204 extending distally therefrom. A tool pathway extends along a longitudinal axis A1 with an opening 206 that is sized to receive an elongate shaft and an end effector of a surgical tool. A person skilled in the art will appreciate that the figures only illustrate a portion of a trocar, namely a mating feature for enabling the trocar to mount to the trocar support. The illustrated mating feature can be utilized on any trocar known in the art. Thus, while not shown, the trocar housing can include one or more seals disposed therein for sealing the tool pathway and/or for forming a seal around an instrument disposed through the tool pathway. The trocar can include other features such as an insufflation port for delivering an insufflation fluid through the tool pathway and into a body cavity.

Figure 2A:
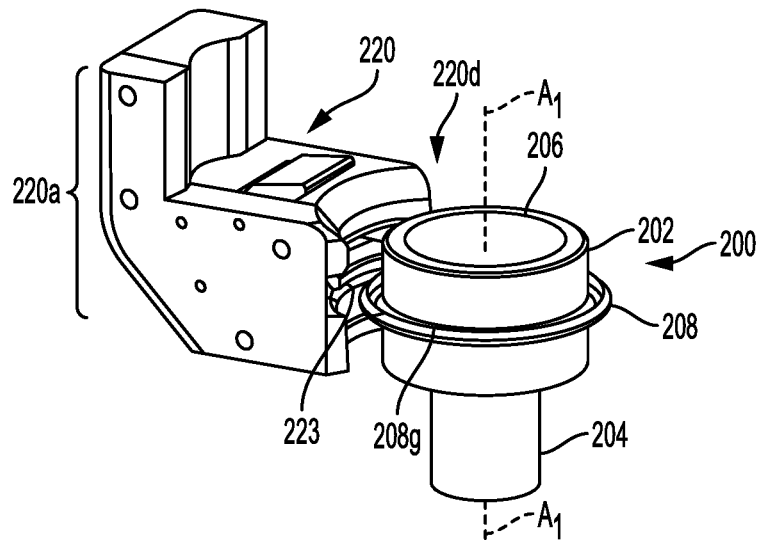
FIG. 2A is a perspective view of one embodiment of a trocar support for engaging a trocar.
Figure 2B:
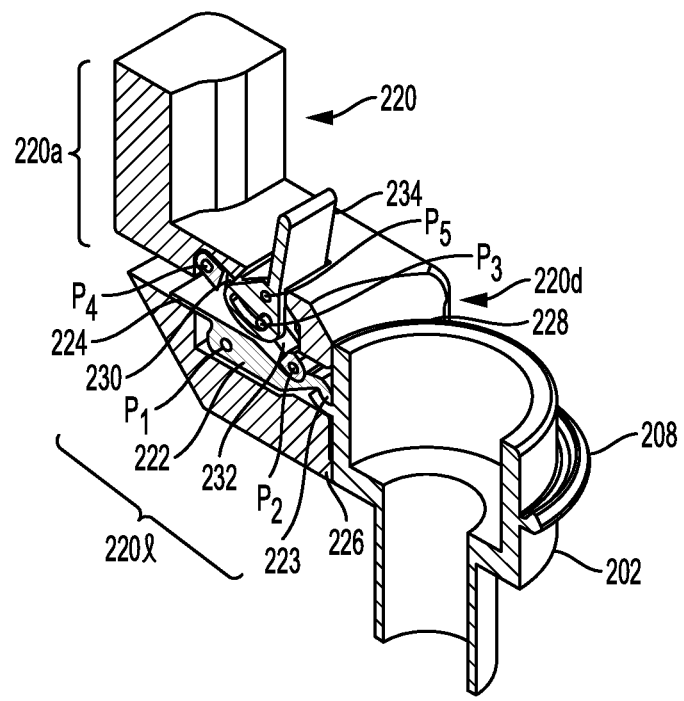
FIG. 2B is a cross-sectional perspective view of the trocar support and trocar of FIG. 2A.
Figure 2C:
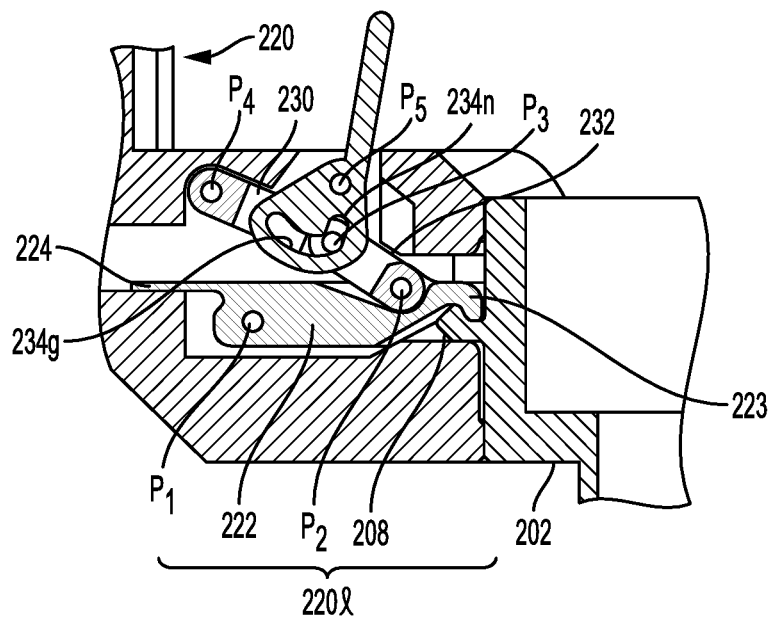
FIG. 2C is a cross-sectional side view of the trocar support and trocar of FIG. 2A.
Figure 2D:
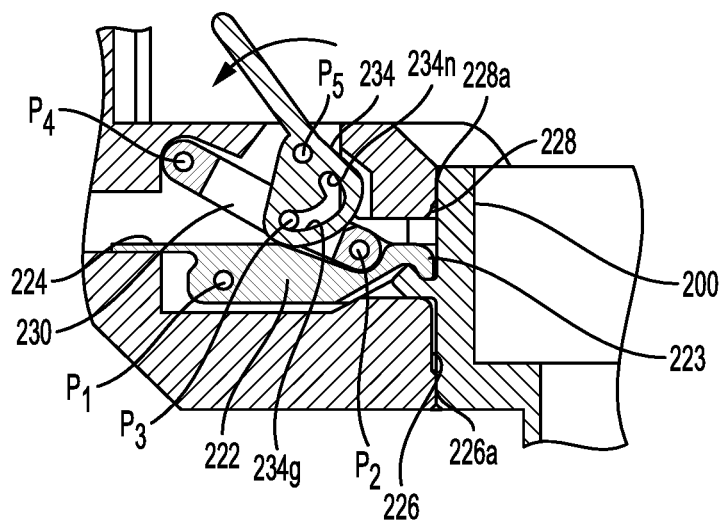
FIG. 2D is a cross-sectional side view of the trocar support and trocar of FIG. 2A.

In this embodiment, the trocar 200 includes a mating ridge or ring 208 positioned radially around an outer circumference of the housing 202. The ring 208 defines a groove 208*g* in an upper surface thereof that is configured to mate with a corresponding hooked clamp arm 222 formed on the trocar support 220. The illustrated trocar support 220 has an approximate L shape, with an upper portion 220*u* that can be formed on or mated to a surgical robotic arm, e.g., a carrier on a distal end of a robotic arm. The trocar support 220 also has a lower portion 220*l* with a distal-most end 220*d* that defines a generally hemi-cylindrical concavity for seating an outer perimeter of the housing 202. The hooked clamp arm 222 can be in the form of an elongate body that extends horizontally through at least a portion of the lower portion 220*l*, and it can include an engagement feature 223 on the terminal end thereof that has a shape corresponding to a shape of the groove 208*g* defined by the ring 208 for grasping the ring 208. The hooked clamp arm 222 can be movable between a neutral or first position, in which the hook extends horizontally, and the engagement feature 223 is positioned within the groove 208*g*, as illustrated in FIG. 2C, and a clamped or second position, in which the hooked clamp arm 222 is forcibly pivoted downward against the groove 208*g*, as illustrated in FIG. 2D. As shown in FIG. 2B, the hooked clamp arm 222 can be pivotal about a pivot point P1. The hooked clamp arm 222 can also be biased into the first position. While various biasing techniques can be used, in the illustrated embodiment the proximal end of the hooked clamp arm 222 can include a biasing spring 224 in the form of a flexible planar member that extends across a surface of the lower portion 220*l* of the support 220. As the trocar 200 is moved into the concavity of the lower portion 220*l*, a force can overcome the biasing spring 224 causing it to flex, thereby allowing the hooked clamp arm 222 to pivot upward about pivot point P1. Once the ring 208 is moved past the engagement feature 223, the biasing spring 224 will cause the hooked clamp arm 222 to move downward thereby causing the engagement feature 223 to extend into the groove 208*g*. A side surface of the trocar housing 202 will rest against an upper lip 228 and a lower lip 226 of the trocar support 220. At this point, the trocar 200 will be attached to the trocar support 220, but the trocar 200 will be freely rotatable around its longitudinal axis A1. The hooked clamp arm 222 will engage the ring 208 and maintain the trocar 200 on the trocar support 220, however nothing will lock the trocar 200 into place. Thus the trocar can be repositioned, for example rotated to allow a user to rearrange the trocar to prevent insufflation tubing from getting in the way during use.

In order to move the trocar support 220 to the locked configuration, in which movement (such as rotation) of the trocar 200 is prevented, the trocar support 220 can include a locking assembly. As shown in FIGS. 2A-2E, the support 220 can include an outer linkage 230, an inner linkage 232, and a locking lever 234. The illustrated locking lever 234 has an approximately triangular base with a lever arm, which protrudes from and is accessible from a top surface of the lower portion 220*l*. However the shape of the locking lever can vary, taking on any convenient geometry to provide the appropriate mechanical advantage. The locking lever 234 can have a semicircular cut-out 234*g* on a distal end of the triangular portion with a notch 234*n* formed on one end of the cut-out 234*g* closest to the trocar. The cut-out 234*g* can be configured to receive a pivot bar therein.

Figure 2E:
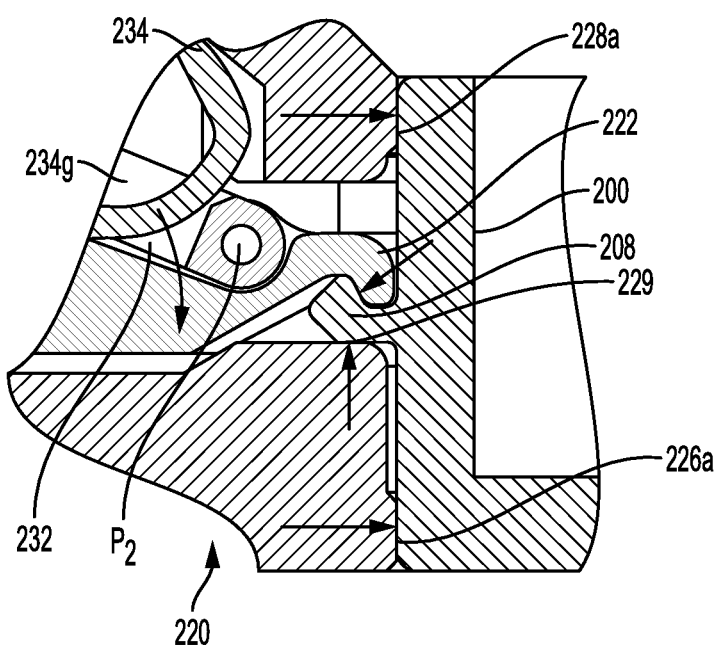
FIG. 2E is a cross-sectional side view of the trocar support and trocar of FIG. 2A.

The hooked clamp arm 222 can be pivotably connected to the inner linkage 232 about pivot point P2, the inner linkage 232 can be pivotably connected to the outer linkage 230 about pivot point P3, the outer linkage 230 can be pivotably connected to the trocar support 220 about pivot point P4, and the locking lever 234 can be pivotable about pivot point P5. The cut-out 234*g* of the locking lever 234 can receive a pivot bar (not shown) defining pivot point P3, and the pivot bar for pivot point P3 can be slidable therein. When the locking lever 234 is in the neutral position, as illustrated in FIG. 2C, the hooked clamp arm 222 can engage the trocar 200 in a manner that mates the trocar 200 to the support 220 while allowing free rotation of the trocar 200 about its longitudinal axis A1. The pivot point P3 is located in a distal end of the cut-out 234*g* toward the trocar 200, but is not received within the notch 234*n*. The biasing spring 224 on the hooked clamp arm 222 keeps the hooked clamp arm 222 biased into this neutral position. To move the locking lever 234 to the locked position, as illustrated in FIG. 2D, the locking lever 234 is pivoted counter-clockwise about pivot point P5 to cause the cut-out 234*g* of the locking lever 234 to engage and force pivot point P3 downward. As pivot point P3 moves downward, linkages 230, 232 are urged into a co-planar configuration, causing the hooked clamp arm 222 to further rotate and impart a maximum clamping load onto the inner surface of the ring 208. Movement of the linkages 230 and 232 is limited by the cross bar defining pivot point P3 in the cut-out 234*g*. In an alternative embodiment, this limit can be adjusted to allow the linkage to travel slightly "over center" and thus become self-locking. Because of the angled inner surface of the hooked clamp arm 222 being forced into engagement with the angled inner surface of the ring 208, the upper lip 228 and the lower lip 226 of the trocar support 220 will press firmly against the side surface of the trocar housing 202. In this position, friction between the trocar support 220 and the trocar 200 is sufficient to prevent rotation of the trocar 200 about its longitudinal axis A1, thereby locking the trocar 200 in a fixed position with respect to the trocar support 220, as illustrated in FIGS. 2D-E.

Figure 2F:
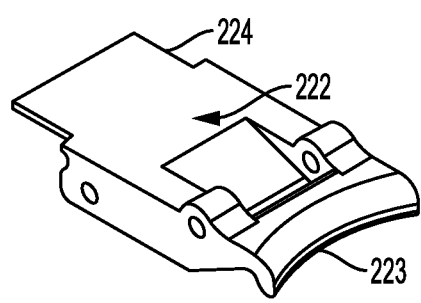
FIG. 2F is a top perspective view of a hooked clamp arm of the trocar support of FIG. 2A.
Figure 2G:
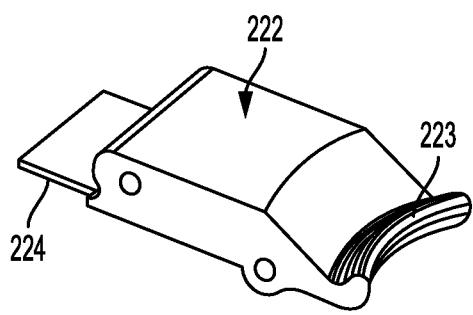
FIG. 2G is a bottom perspective view of the hooked clamp arm of FIG. 2F.

To enhance stability performance of the locking mechanism, raised pads 228a, 226a can be located on the outer edges of the upper and lower lips 228, 226 to maximize resistance to rotation of the trocar 200, thus providing several friction points at which the trocar 200 and the trocar support 220 will be engaged with each other. For example as illustrated in FIG. 2E, friction points can be formed between the raised pads 228a, 226a and the trocar 200, the hooked clamp arm 222 and the ring 208, and the ring 208 and a surface 229 of the trocar support 220. While a locking lever 234 is illustrated, for example as shown in FIGS. 2F and 2G, a variety of locking mechanisms can be used, such as levers, buttons, knobs, etc.

In other embodiments, the groove 208g on the ring 208 can have rounded or angled distal edges that are angled away from the hooked clamp arm 222 so that, as the ring 208 is pushed into contact with the hooked clamp arm 222, the hooked clamp arm 222 can slide along the angled surfaces of the engagement feature 208g and cause the hooked clamp arm 222 to raise and accept insertion of the ring 208 before lowering into engagement with the ring 208. A user may thus simply push the trocar 200 into engagement with the trocar support 220. The engagement feature 208g on the ring 208 can also have rounded or angled interior edges such that the hooked clamp arm 222 can slide along the angled surfaces during removal.

A user may remove the trocar 200 from engagement with the trocar support 220 by applying a force to the trocar to overcome the force of the biasing spring 224 on the hooked clamp arm 222, allowing the hooked clamp arm 222 to rotate upward to disengage from the ring 208 while the pivot point P3 can be simultaneously received in the notch 234n to facilitate removal in a similarly quick and simple process. Multiple mechanisms exist that can lock rotation, such as rotation about pivot point P1, and the mechanism discussed herein is just one example of one such mechanism. The rotation-locking mechanism is not limited to just the one shown.

Figure 3A:
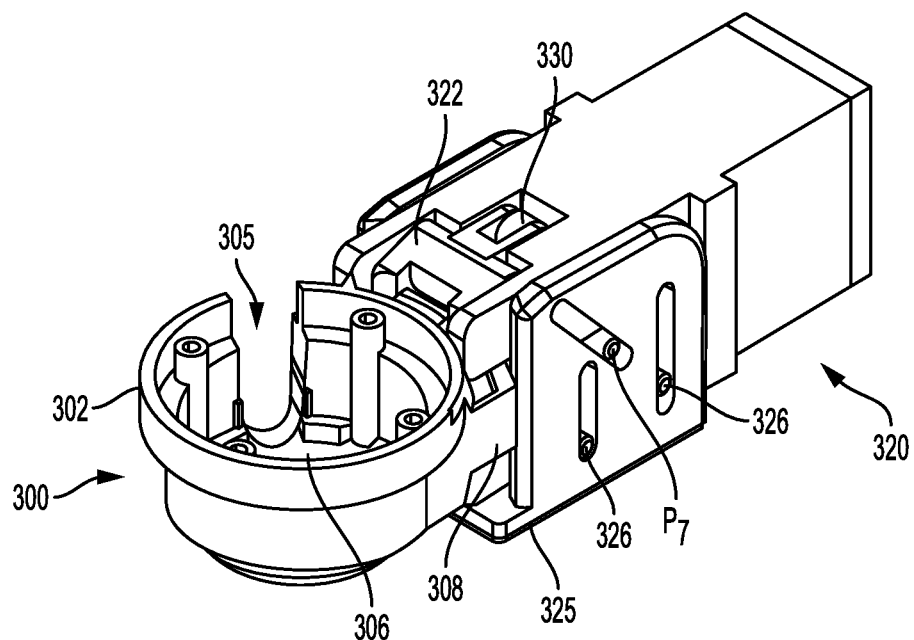
FIG. 3A is a perspective view of another embodiment of a trocar engaging a trocar support.
Figure 3B:
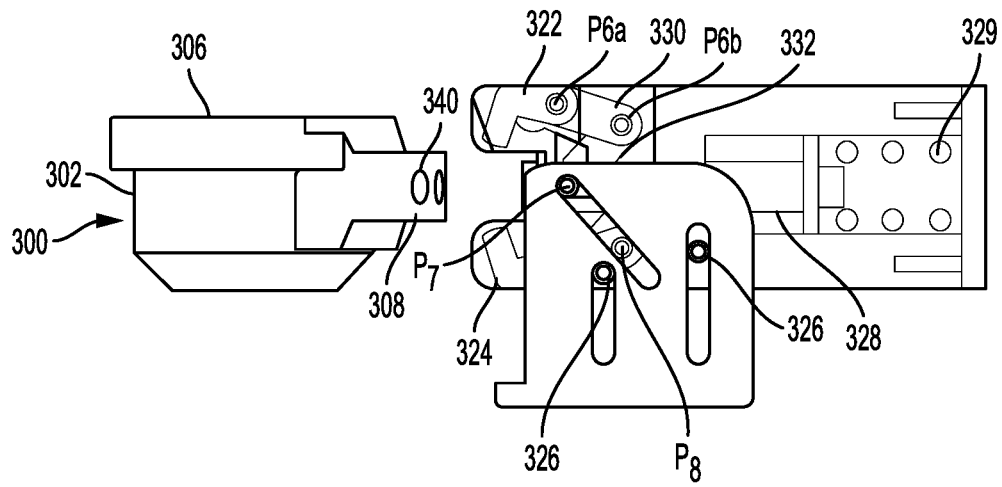
FIG. 3B is a side, partially cross-sectional view of the trocar and the trocar support of FIG. 3A not engaged with each other.
Figure 3C:
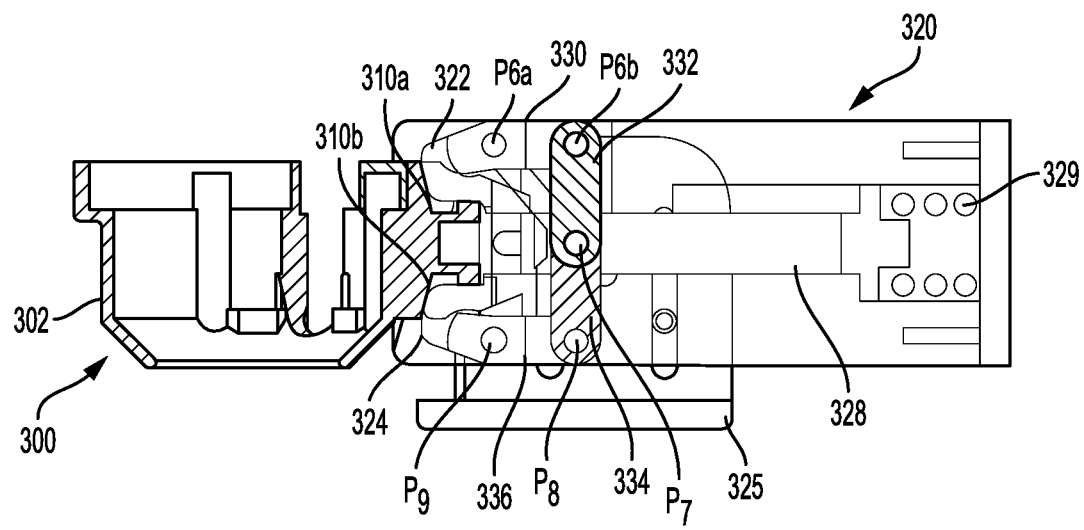
FIG. 3C is a side, partially cross-sectional view of the trocar and the trocar support of FIG. 3A engaged with each other.
Figure 3D:
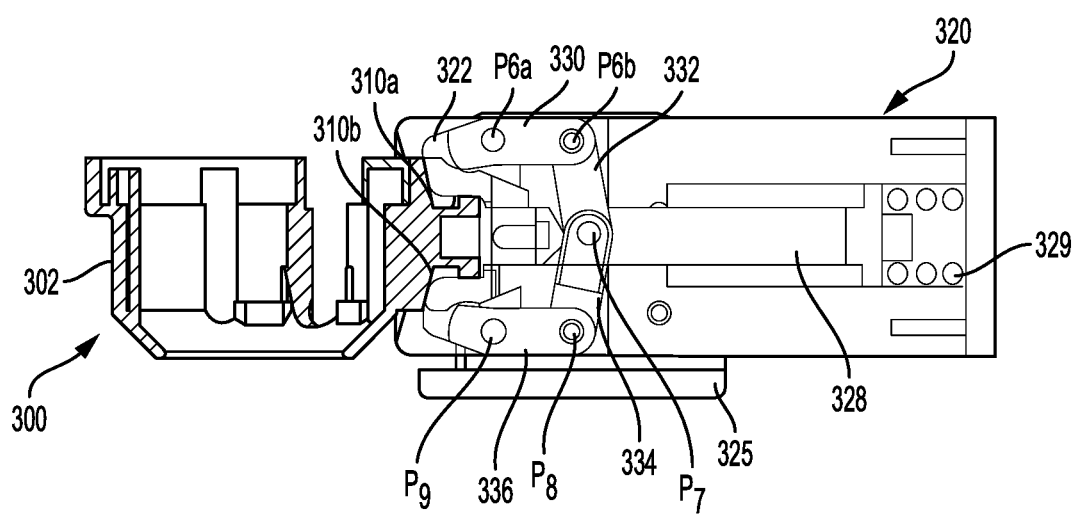
FIG. 3D is a side, partially cross-sectional view of the trocar and the trocar support of FIG. 3A engaged with each other.

FIGS. 3A-3F illustrate another embodiment of a trocar 300 and a trocar support 320 configured to engage the trocar 300 in first and second configurations. The trocar 300 can have a configuration as discussed above with respect to FIGS. 2A-2C, and generally includes a housing 302 having a cannula (not shown) extending therefrom. The illustrated trocar includes a cut-out, receiver, and/or notch 305 formed in a sidewall of the housing 302 to accommodate an insufflation tubing. In this embodiment, rather than a ring, the trocar includes a protrusion 308 projecting from the sidewall of the housing 302 and having grooves 310a, 310b formed in upper and lower surfaces thereof (as illustrated in FIGS. 3C-3D). The protrusion 310 is configured to be received in a recess formed in the trocar support 320, and the grooves 310a, 310b are configured to be engaged by a pair of upper hooks 322 and a pair of lower hooks 324 on the trocar support 320. The upper hooks 322 and the lower hooks 324 are connected to each other by a series of linkages 330, 332, 334, 336 and pivot bars P6a, P6b, P7, P8, P9. As will be discussed in more detail below, the linkages 330, 332, 334, 336 and pivot bars P6a, P6b, P7, P8, P9 are configured to cause movement of the upper and lower hooks 322, 324 between a disengaged position, where the hooks 322, 324 are configured to receive the protrusion 308 on the trocar 300, and an engaged position in which the hooks 322, 324 extend into the grooves 310a, 310b to engage the protrusion 308.

The trocar support 320 also has a push bar 328 that is spring biased in a distal position (toward the trocar), for example by a compression spring 329, such that a distal-most end of the push bar 328 extends from the trocar support 320 and into the recess that receives the protrusion 308 on the trocar 300. The push bar 328 is also coupled to pivot bar P7, which is disposed midway between the upper hooks 322 and the lower hooks 324 such that the upper hooks 322 are pivotably connected to linkage 330 and linkage 332 and the lower hooks 324 are pivotably connected to linkage 336 and linkage 334. The linkages 332, 334 are pivotably connected to each other and the push bar 328 by the pivot bar P7. A slider 325 having an approximate U-shape extends around both side surfaces and a bottom surface of the trocar support 320. The slider 325 has two vertical slots formed therein that receive two support bars 326, respectively. The slider 325 also has an angled slot extending at an approximate 45 degree angle that receives a pin on the pivot bar P7, as well as a pin on the trocar support 220 that defines pivot point P8.

Figure 3E:
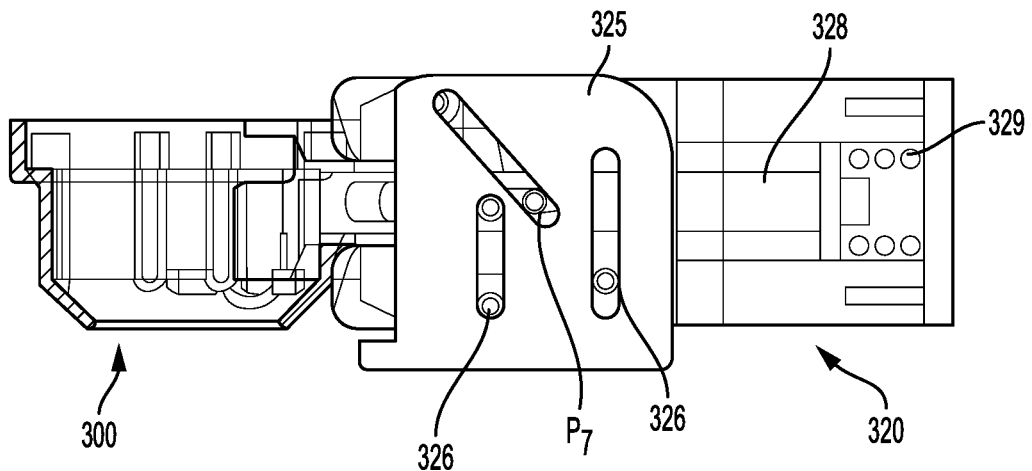
FIG. 3E is a side, partially cross-sectional view of the trocar and the trocar support of FIG. 3A engaged with each other.

As noted above, the upper and lower hooks 322, 324 have an open position, as illustrated in FIG. 3B, in which the hooks 322, 324 are moved away from one another do not engage any structure, the push bar 328 and the pivot bar P7 are both in a distal-most position, and the linkages 332, 334 are in a distal-angled vertical position. The bottom surface of the slider 325 and the bottom surface of the trocar support 320 are spaced a distance away from each other. As the trocar 300 is moved toward the trocar support 320, the protrusion 310 enters the recess on a distal surface of the trocar support 320 and contacts a distal-most end of the push bar 328. As the protrusion 310 continues to push proximally against the push bar 328, the biasing force of the spring 329 is overcome and the push bar 328 slides proximally relative to the trocar support 320. As the push bar 328 slides proximally, the vertical slot causes the pivot bar P7 to slide proximally with the push bar 328, which causes the linkages 332, 334 to pivot first to a vertically aligned position with respect to each other (as illustrated in FIG. 3C), which causes the upper and lower hooks 322, 324 to move together and engage the grooves 310a, 310b of the protrusion 310 and then to a proximal-angled vertical position (as illustrated in FIG. 3D), for example by about 10 degrees from the vertically aligned position. In this position, as a result of the linkages 332, 334 being angled proximally on their outward ends, the linkages 332, 334 will resist distal movement, resulting in the trocar 300 being locked in a fixed position relative to the trocar support 320. The linkages 332, 334 will resist the biasing force of the spring 329 and maintain the trocar 300 in engagement with the trocar support 320 through the action of the hooks 322, 324 in the grooves 310a, 310b of the protrusion 310. During this motion, the bottom surface of the slider 325 moves toward the bottom surface of the trocar support 320 as the slider slides with the motion of the pivot bar P7 until the bottom surface of the slider 325 is positioned against the bottom surface of the trocar support 320, as illustrated in FIG. 3E. The trocar 300 will remain attached to the trocar support 320 until a user presses down on the slider 325 to cause the push bar 328 to move distally again, assisted by the compression spring 329, and causing the hooks 322, 324 to disengage from the grooves 310a, 310b and the push bar 328 to force the protrusion 310 distally out of the recess in the trocar support 320.

Figure 3F:
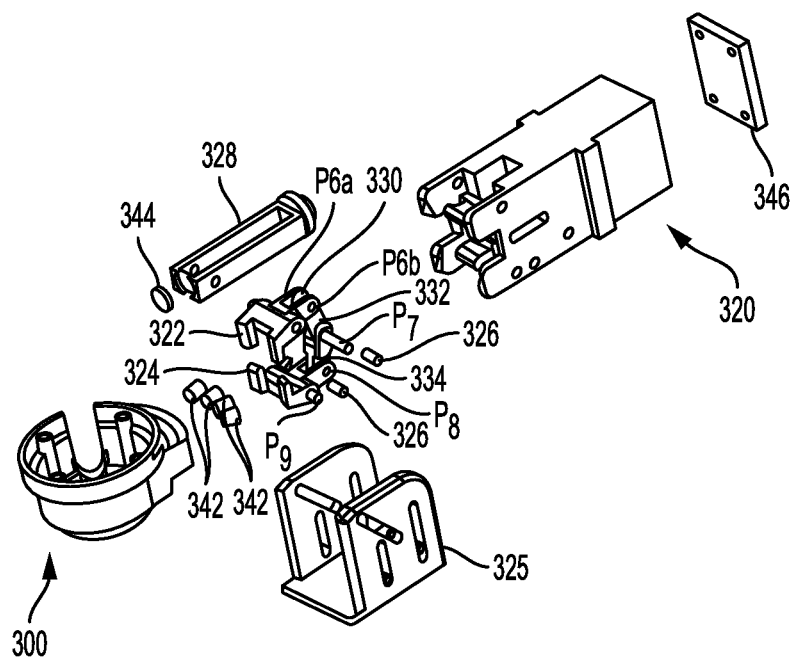
FIG. 3F is an exploded view of the trocar and the trocar support of FIG. 3A.

The grooves 310a, 310b can vary in length, which can allow the trocar 300 to be freely rotated about its longitudinal axis. For example, the grooves 310a, 310b can be long enough to allow the trocar 300 to be rotated by about 15 degrees. The protrusion 310 can also have magnets 340 disposed on or in a proximal surface thereof, and the trocar support can have corresponding magnets 342 on or in a distal surface thereof to assist with aligning the protrusion 310 with the recess in the trocar support 320. Magnet 344 can be attached to a distal-most end of the push bar 328 to assist with alignment and contact, and an attachment plate 346 can attach to a proximal-most end of the trocar support 320 to assist in attaching the trocar support 320 to a robotic arm, as illustrated in FIG. 3F. Additionally the hooks 322, 324 can have distal surfaces that are angled away from the protrusion 310 so that, as the protrusion 310 is inserted into the recess of the trocar support 320, the protrusion 310 can slide along the angled surfaces of the hooks 322, 324 and cause the hooks 322, 324 to raise and accept insertion of the protrusion 310 before lowering into engagement with the grooves 310a, 310b. A user may thus simply push the trocar 300 into engagement with the trocar support 320.

Figure 4A:
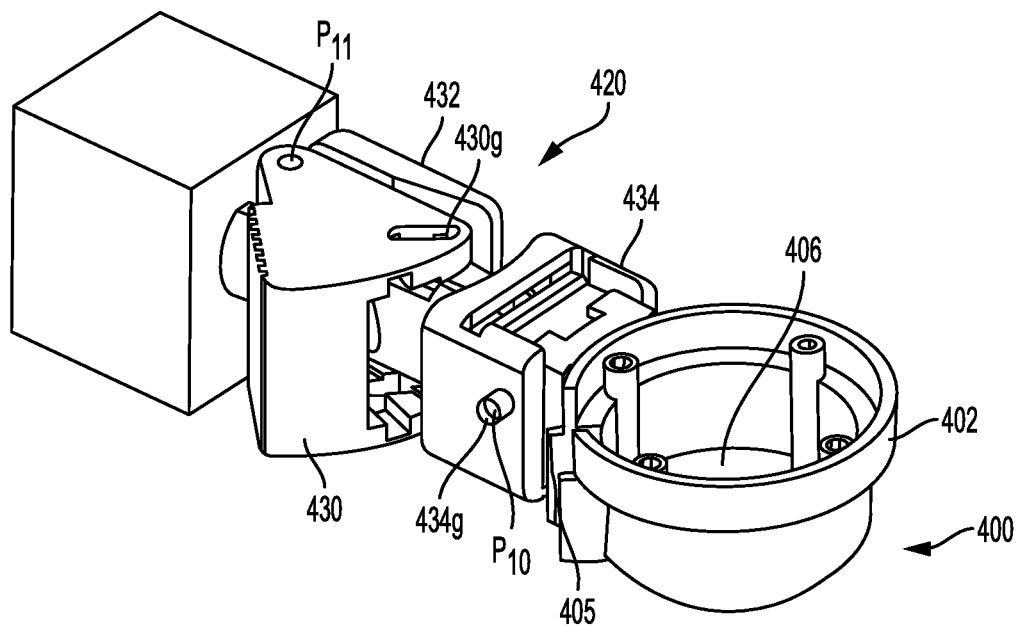
FIG. 4A is a perspective view of another embodiment of a trocar engaging a trocar support.
Figure 4B:
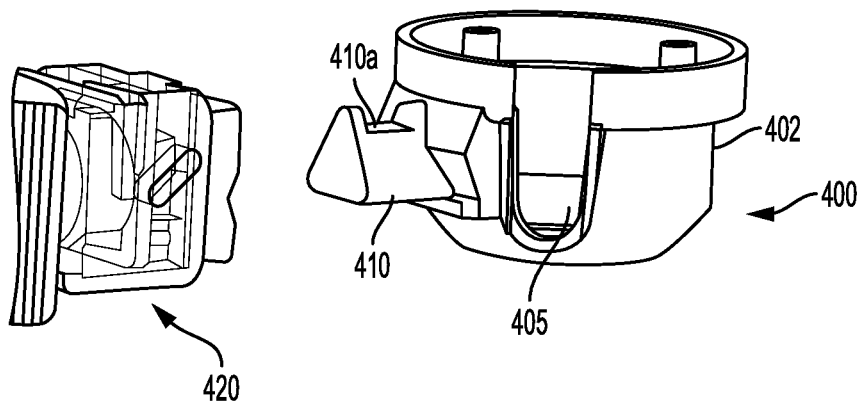
FIG. 4B is a perspective view of the trocar and the trocar support of FIG. 4A.
Figure 4C:
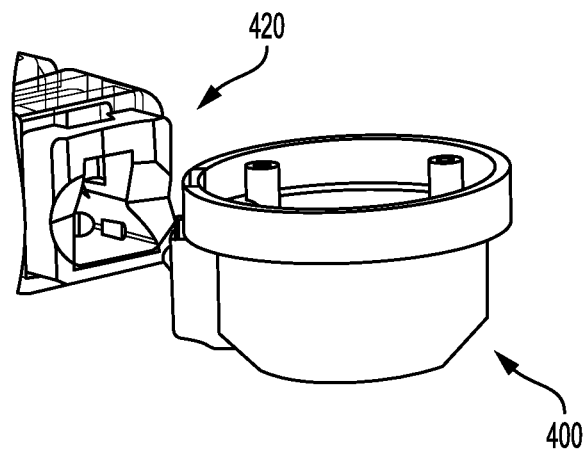
FIG. 4C is a perspective view of the trocar and the trocar support of FIG. 4A.
Figure 4D:
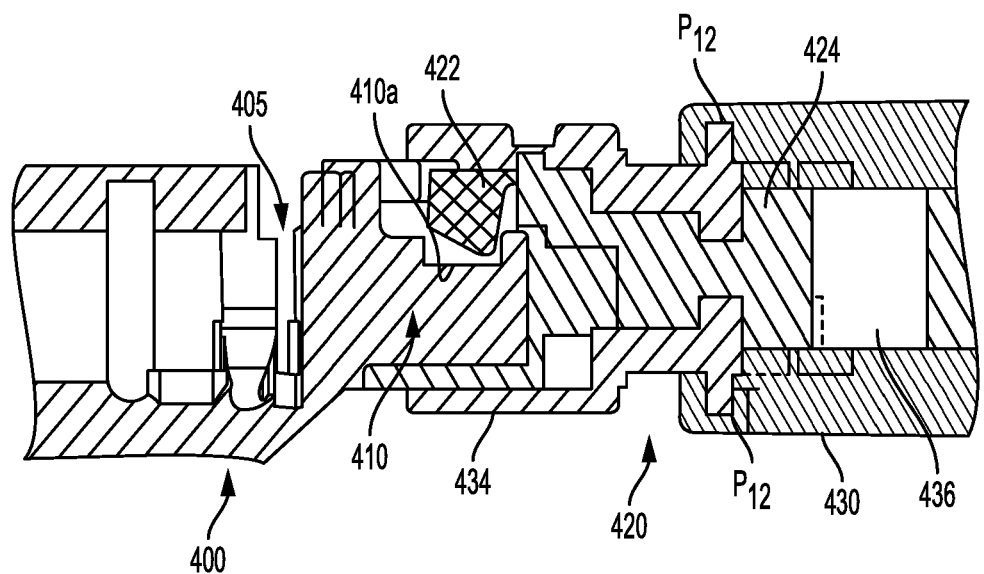
FIG. 4D is a side, cross-sectional view of the trocar and the trocar support of FIG. 4A.
Figure 4E:
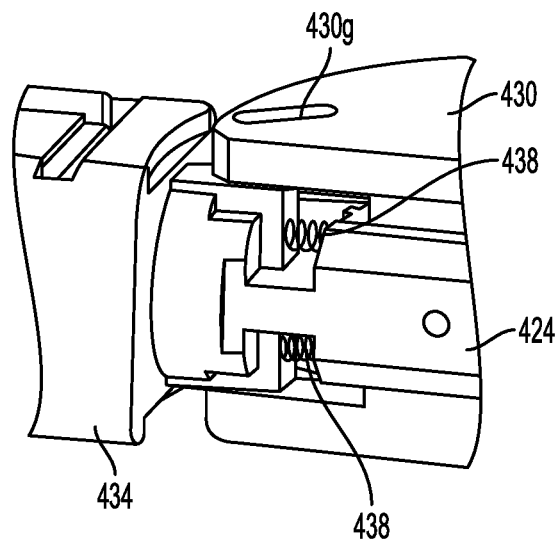
FIG. 4E is a perspective view of the trocar and the trocar support of FIG. 4A.
Figure 4F:
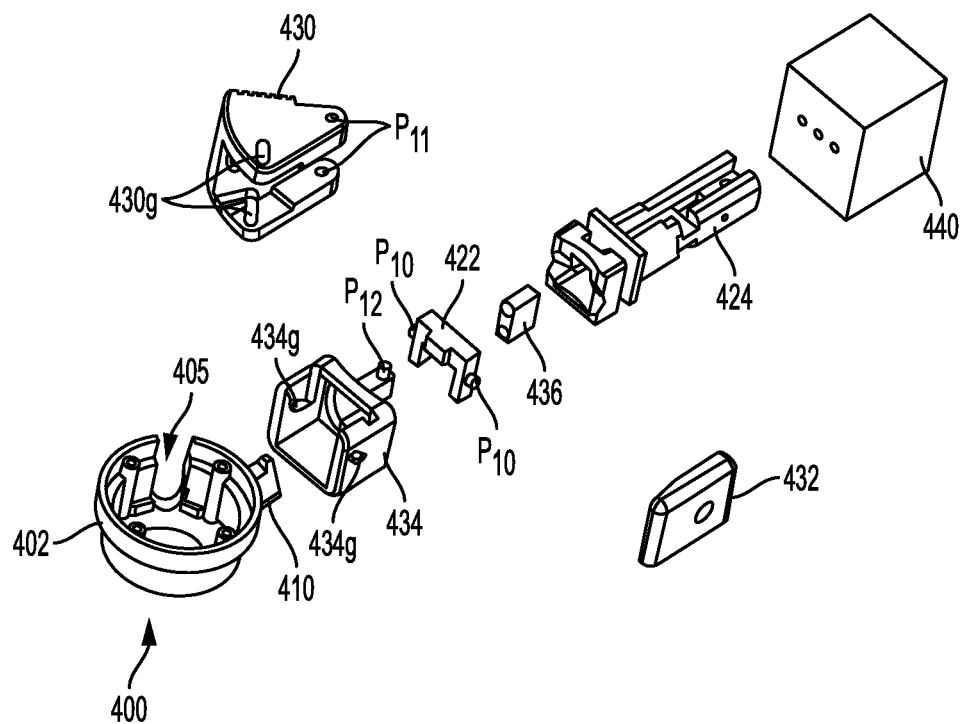
FIG. 4F is an exploded view of the trocar and the trocar support of FIG. 4A.

FIGS. 4A-4F illustrate another embodiment of a trocar 400 with a housing 402. A tool pathway extends therethrough with an opening 406 that is sized to receive an elongate shaft and an end effector of a surgical tool and a notch 405 is formed in a sidewall of the housing 402 to accommodate insufflation tubing. A protrusion 408 extends proximally from the sidewall of the housing 402 and has a groove 410a formed in an upper surface thereof, as illustrated in FIG. 4B. The protrusion 410 in this embodiment has an approximately triangular cross-sectional shape. The protrusion 410 is received into a triangular-shaped recess formed in a trocar support 420, as illustrated in FIG. 4C. The groove 410a is engaged by upper hook 422 of the trocar support 420. The trocar support 420 has a support base 424 with the recess formed on a distal end thereof, a rotating lever 430, an anchor block 432, and a slider block 434. The upper hook 422 has pivot bars P10 disposed on either side of the upper hook 422 that engage the slider block 434 by being slidably disposed in grooves 434g extending along opposite side surfaces of the slider block 434 at an approximately 45 degree angle. The rotating lever 430 pivots about pivot point P11 with respect to the trocar support 420 and the anchor block 432, and the slider block 434 has pivot bars P12 that engage the rotating lever 430 by being slidably disposed in grooves 430g extending along a top and bottom surface of the rotating lever 430 at an approximately 45 degree angle. Springs 438 rest in spring housing 436 on the support base 424, and the springs 438 bias the slider block 434 distally. By biasing the slider block 434 distally, the pivot bars P10 of the hook 422 are forced toward a bottom of the grooves 434g in the slider block 434 such that the hook 422 is maintained in a lowered or engaged state.

When a user wants to attach the trocar 400 to the trocar support 420, the user squeezes or applies pressure to the rotating lever 430. The rotating lever 430 pivots about pivot point P11 and moves toward the anchor block 432. As the rotating lever 430 moves, the pivot bars P12 of the slider block 434 are forced proximally along the grooves 430g of the rotating lever 430. This proximal movement overcomes the biasing force of the springs 438, and the slider block 434 slides proximally. The proximal movement of the slider block 434 causes the pivot bars P10 of the upper hook 422 to slide upward in the grooves 434g of the slider block 434. The upward movement of the pivot bars P10 causes the hook 422 to rise into a position in which the protrusion 410 of the trocar 400 can be inserted into the recess of the trocar support 420 without contacting the hook 422. When the protrusion 410 is inserted into the recess of the trocar support 420, the rotating lever 430 can be released. The springs 438 will force the slider block 434 distally again, causing the pivot bars P12 of the slider block 434 to slide in the grooves 430g of the rotating lever 430 and force the rotating lever 430 to move away from the anchor block 432. Distal movement of the slider block 434 will also cause the pivot bars P10 of the upper hook 422 to slide within the grooves 434g of the slider block 434 and lower the upper hook 422 to its engaged state, causing the hook 422 to engage the groove 410a of the protrusion 410 of the trocar 400. At this point, the trocar 400 is engaged with the trocar support 420 through the hook 422. To release the trocar 400, the rotating lever 430 can be squeezed again to move the rotating lever 430 toward the anchor block 432, restarting the process described above to cause the hook 422 to rise out of engagement with the groove 410a of the protrusion 410.

The protrusion 410 and the recess formed in the trocar support 420 can have a triangular shape to provide greater restriction of movement of the trocar 400 when attached to the trocar support 420. However, a variety of shapes can be used, such as squares, ovals, etc. Additionally the hook 422 has a distal surface that is angled away from the protrusion 410 so that, as the protrusion 410 is inserted into the recess of the trocar support 420, the protrusion 410 can slide along the angled surface of the hook 422 and cause the hook 422 to open and accept insertion of the protrusion 410 before lowering into engagement with the groove 410a. A user may thus simply push the trocar 400 into engagement with the trocar support 420 and only be required to use the rotating lever 430 when disengaging the two. Supporting structures, lips, ledges, etc. can be incorporated into both distal surfaces of the trocar support 420 and proximal surfaces of the trocar 400 to act as guides and stops as the trocar 400 is inserted into the trocar support 420. An engagement block 440 can be provided to assist in connecting the trocar support 420 to a robotic arm.

Figure 5A:
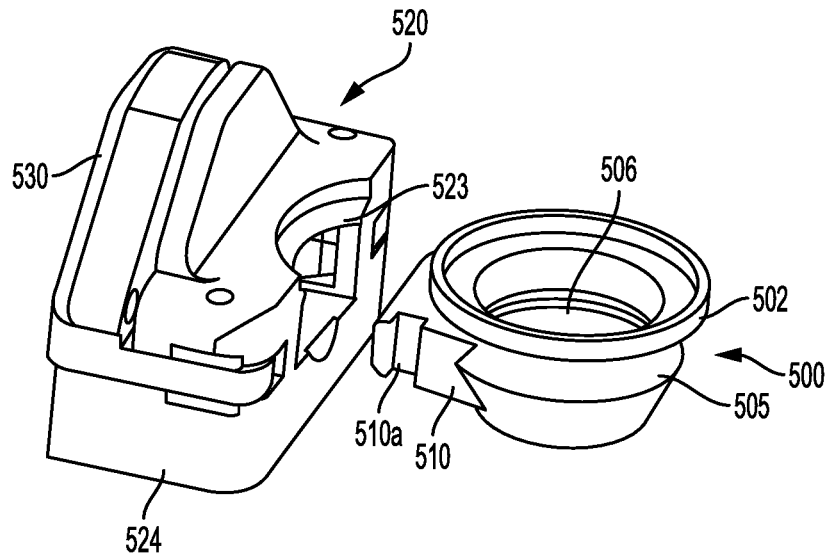
FIG. 5A is a perspective view of another embodiment of a trocar engaging a trocar support.
Figure 5B:
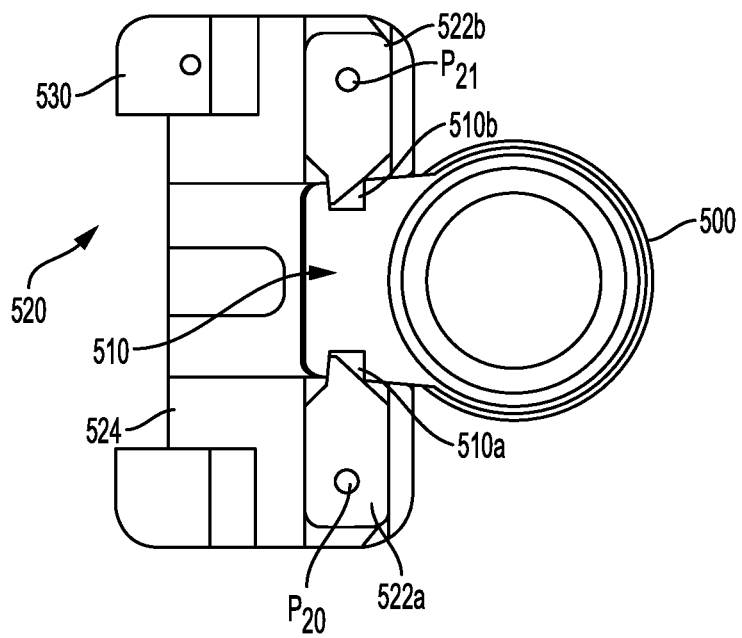
FIG. 5B is a cross-section top-down view of the trocar and the trocar support of FIG. 5A.
Figure 5C:
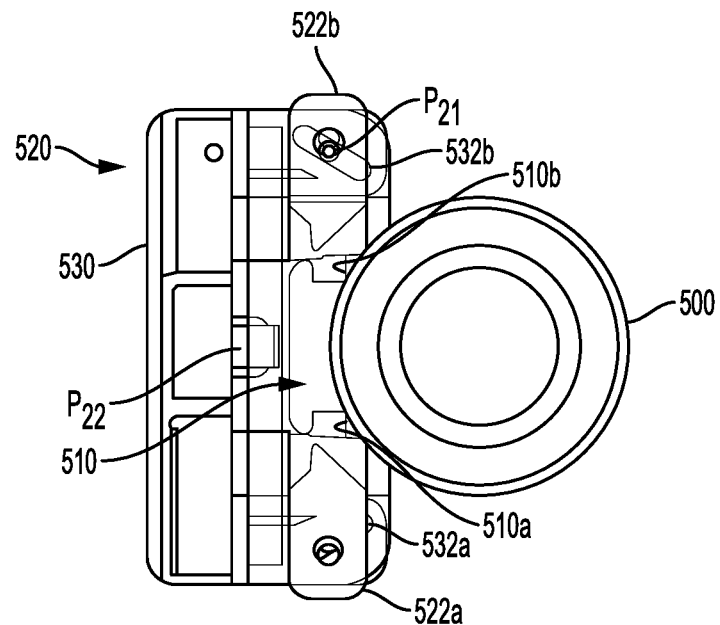
FIG. 5C is a partially transparent top-down view of the trocar and the trocar support of FIG. 5A.
Figure 5D:
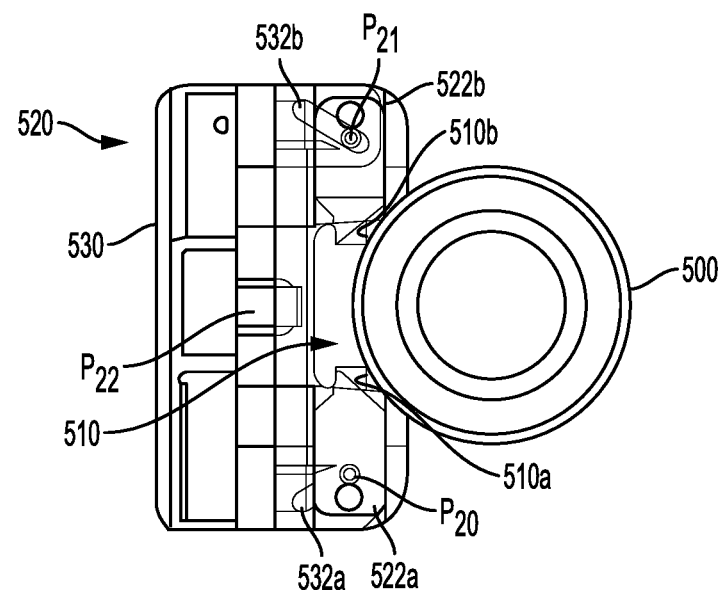
FIG. 5D is a partially transparent top-down view of the trocar and the trocar support of FIG. 5A.
Figure 5E:
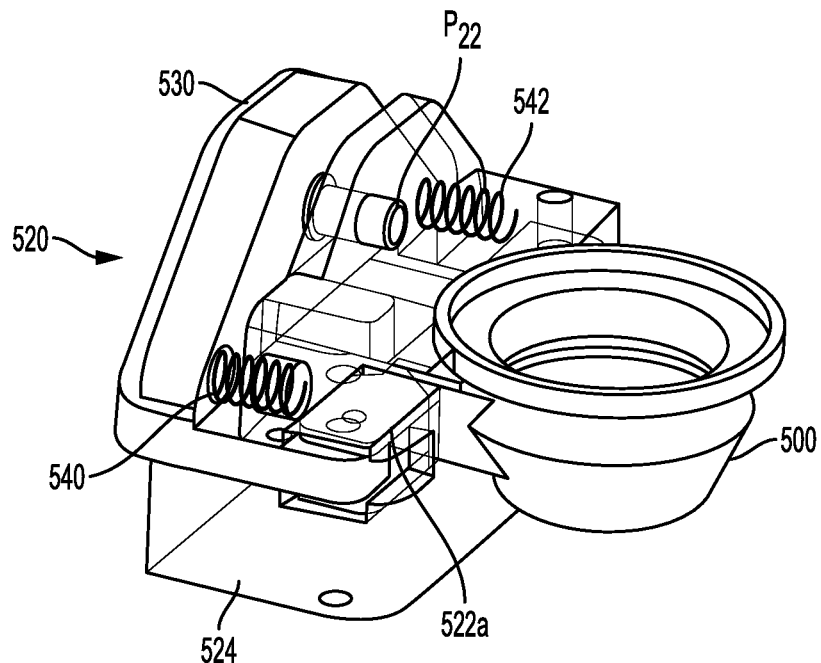
FIG. 5E is a partially transparent perspective view of the trocar and the trocar support of FIG. 5A.
Figure 5F:
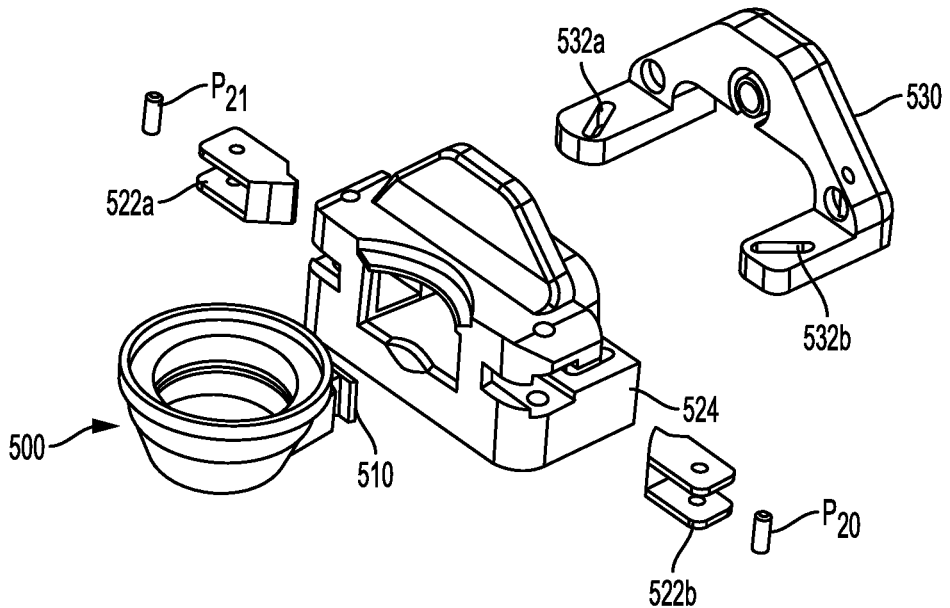
FIG. 5F is an exploded view of the trocar and the trocar support of FIG. 5A.

FIGS. 5A-5F illustrate another embodiment of a trocar 500 with a housing 502. A tool pathway extends therethrough with an opening 506 that is sized to receive an elongate shaft and an end effector of a surgical tool. A protrusion 508 extends proximally from the sidewall of the housing 502 and has grooves 510a, 510b formed on either sidewall of the protrusion 508, as illustrated in FIG. 5B. The protrusion 510 in this embodiment has an approximately rectangular cross-section. The protrusion 510 is received into a rectangular-shaped recess formed in a trocar support 520. The trocar 500 has a lip 505 that is received onto a corresponding lip 523 on the trocar support 520 to provide additional support and structural engagement between the trocar 500 and the trocar support 520. The grooves 510a, 510b are engaged by first and second hook sliders 522a, 522b disposed in slots in the trocar support 520. The trocar support 520 has a support base 524 with the recess formed on a distal end thereof and a U-shaped or horseshoe-shaped sliding lever 530 that engages the first and second hook sliders 522a, 522b through pivot bars P20, P21. The pivot bars P20, P21 sit in grooves 532a, 532b in the sliding lever 530 that are angled at approximately 45 degrees. The sliding lever 530 has an alignment pin P22 that keeps the sliding lever 530 aligned with the trocar support 520 while allowing the sliding lever 530 to slide distally and proximally. Springs 540, 542 are disposed between the sliding lever 530 and the trocar support 520, as illustrated in FIG. 5E, and they bias the sliding lever 530 to a proximal-most position with respect to the trocar support 520. Because the pivot pins P20, P21 sit in the angled grooves 532a, 532b, when the sliding lever 530 is biased to a proximal-most position, the pivot pins P20, P21 are forced into a distal, inner end of the angled grooves 532a, 532b, which causes the first and second hook sliders 522a, 522b to move toward a center of the trocar support 520 into an engaged position with the first and second hook sliders 522a, 522b extending into the recess of the trocar support 520.

When attaching the trocar 500 to the trocar support 520, the sliding lever 530 can be moved distally to overcome the spring bias of the springs 540, 542. As the sliding lever 530 moves distally, the pivot pins P20, P21 will slide in the angled grooves 532a, 532b of the sliding lever 530, which will force the pivot pins P20, P21 into a proximal, outer position in the angled grooves 532a, 532b away from the recess of the trocar support 520. This movement will cause the first and second hook sliders 522a, 522b to slide out of the recess and into a disengaged position. The protrusion 510 can then be inserted into the recess of the trocar support 520 without the protrusion 510 contacting the first and second hook sliders 522a, 522. When the protrusion 510 is entirely disposed within the recess, the sliding lever 530 can be released, causing the springs 540, 542 to bias the sliding lever 530 proximally again. Proximal movement of the sliding lever 530 will cause the pivot pins P20, P21 to move distally and inward along the angled grooves 532a, 532b, causing the first and second hook sliders 522a, 522b to re-enter the recess and engage the grooves 510a, 510b of the protrusion 510 so that the trocar 500 will be attached to the trocar support 520. The trocar 500 can be released from the trocar support 520 by moving the sliding lever 530 distally again.

The first and second hook sliders 522a, 522b can have distal surfaces that are angled away from the protrusion 510 so that, as the protrusion 510 is inserted into the recess of the trocar support 520, the protrusion 510 can slide along the angled surface of the first and second hook sliders 522a, 522b and cause the first and second hook sliders 522a, 522b to slide outward to accept insertion of the protrusion 510 before sliding toward the recess again into engagement with the grooves 510a, 510b. A user may thus simply push the trocar 500 into engagement with the trocar support 520 and only be required to use the sliding lever 530 when disengaging the two. Supporting structures, lips, ledges, etc., such as a dimple formed on a distal edge of the trocar support 520 for receiving part of the trocar 500, can be incorporated into both distal surfaces of the trocar support 520 and proximal surfaces of the trocar 500 to act as guides and stops as the trocar 500 is inserted into the trocar support 520.

Figure 6A:
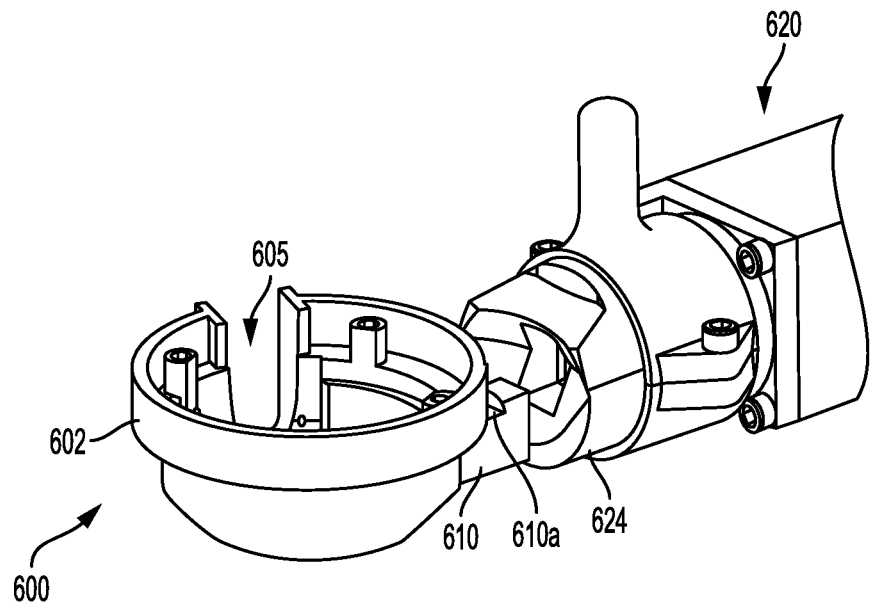
FIG. 6A is a perspective view of another embodiment of a trocar engaging a trocar support.
Figure 6B:
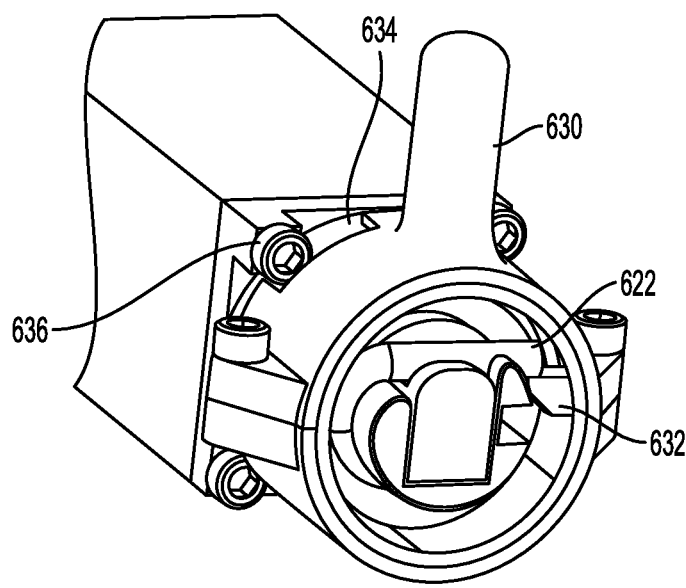
FIG. 6B is a partial cross-sectional perspective view of the trocar and the trocar support of FIG. 6A.
Figure 6C:
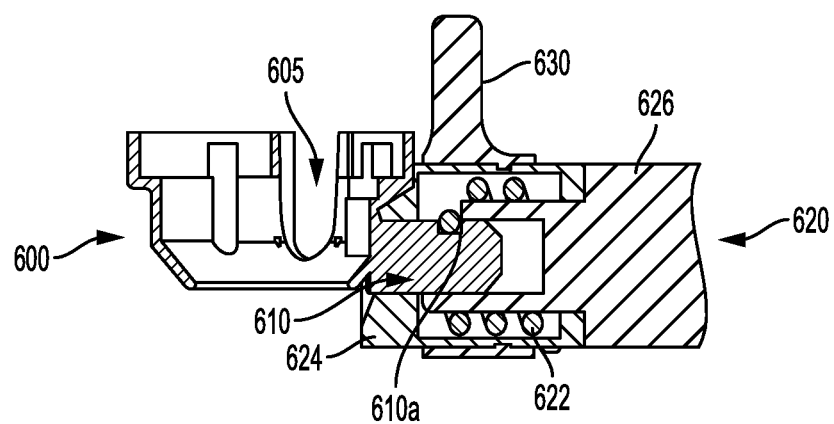
FIG. 6C is a partial cross-sectional side view of the trocar and the trocar support of FIG. 6A.

FIGS. 6A-6C illustrate another embodiment of a trocar 600 with a housing 602. A tool pathway extends therethrough with an opening 606 that is sized to receive an elongate shaft and an end effector of a surgical tool, and a notch 605 is formed in a sidewall thereof to receive insufflation tubing. A protrusion 608 extends proximally from the sidewall of the housing 602 and has a groove 610a formed on a top surface thereof. In this embodiment, the protrusion 610 has an approximately square cross-sectional shape. The protrusion 610 is received into a square-shaped recess formed in a trocar support 620. The trocar 600 has notches and a lip formed on a proximal side of the protrusion 610 that are received onto corresponding ledges and a lip on the trocar support 620 to provide additional support and structural engagement between the trocar 600 and the trocar support 620. The groove 610a is engaged by a spring hook 622 disposed within a cylindrical recess of the trocar support 620. The trocar support 620 has a distal structure 624 with the recess formed therein and a rotating lever 630 that is rotatably engaged with the trocar support 620. The spring hook 622 has a straight distal-most end that is configured to sit in the groove 610a of the protrusion 610. The spring hook 622 can be biased toward the groove 610a into an engaged position. The spring hook 622 coils around a proximal portion 626 of the trocar support 620 and sits within a recess formed in the distal portion 624. The rotating lever 630 extends around a circumference of the distal portion 624 of the trocar support 620 and is rotatable around a longitudinal axis of the trocar support 620. A tab 632 attached to the rotating lever 630 extends through the distal portion 624 of the trocar support and contacts the distal-most end of the straight end of the spring hook 622. The rotating lever 630 is configured to rotate so that the tab 632 lifts the straight end of the spring hook 622 upwards, moving the straight end of the spring hook 622 into an unengaged position. The rotating lever 630 has one or more grooves 634 on an outer surface into which one or more nuts 636 can fit that are attached to the trocar support 620. As the rotating lever 630 is rotated, the nut 636 will slide around in the groove 634 until the nut 636 contacts one of the two ends of the groove 634, preventing over-rotation of the rotating lever 630.

When attaching the trocar 600 to the trocar support 620, the protrusion 610 is inserted into the recess of the trocar support 620. A proximal end of the protrusion 610 is angled such that the straight end of the spring hook 622 will slide upwards along the angled end of the protrusion 610 until the straight end of the spring hook 622 falls into engagement with the groove 610a. At this point, the trocar 600 and the trocar support 620 are attached to one another. When it is desired to disconnect the trocar 600 and the trocar support 620, the rotating lever 630 can be rotated to cause the tab 632 to lift the straight end of the spring hook 622 upwards, thereby moving the straight end of the spring hook 622 out of the groove 610a and into an unengaged position. The trocar 600 can then be removed from the trocar support 620. The trocar support 620 can also incorporate a second spring that biases the rotating lever 630 to an engaged position for the straight end of the spring hook 622 so that rotating the lever 630 to move the straight end of the spring hook 622 into an unengaged position requires overcoming the spring bias of the second spring.

Figure 7A:
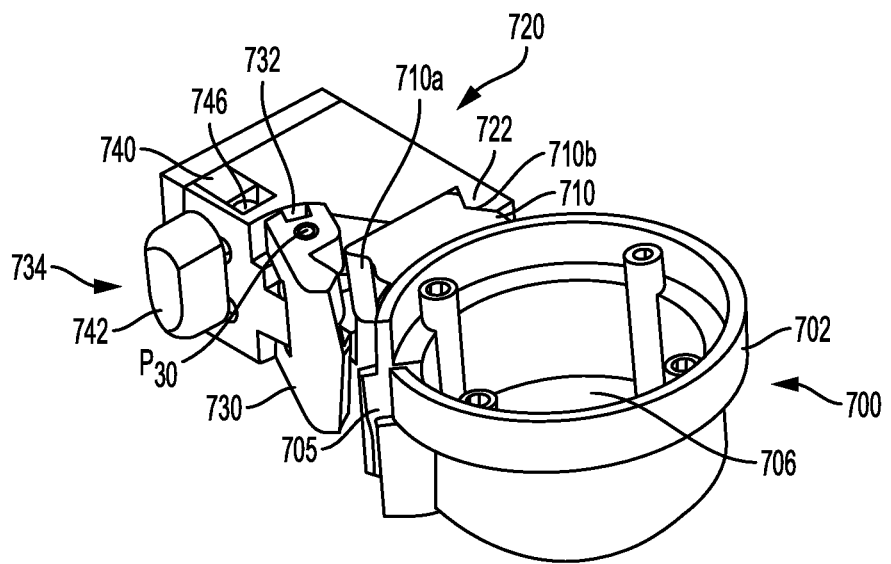
FIG. 7A is a perspective view of another embodiment of a trocar engaging a trocar support.
Figure 7B:
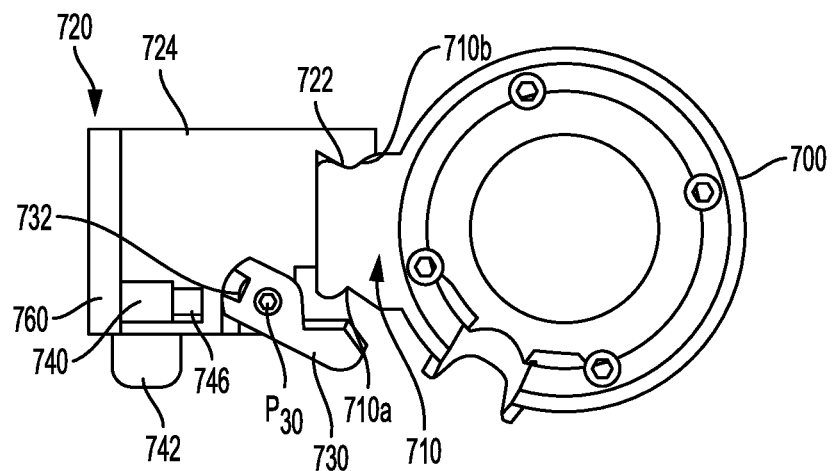
FIG. 7B is a top-down view of the trocar and the trocar support of FIG. 7A.
Figure 7C:
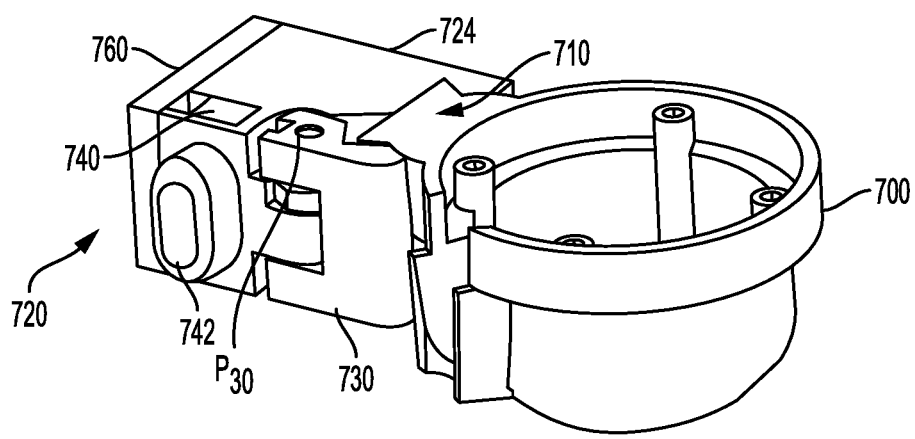
FIG. 7C is a perspective view of the trocar and the trocar support of FIG. 7A.
Figure 7D:
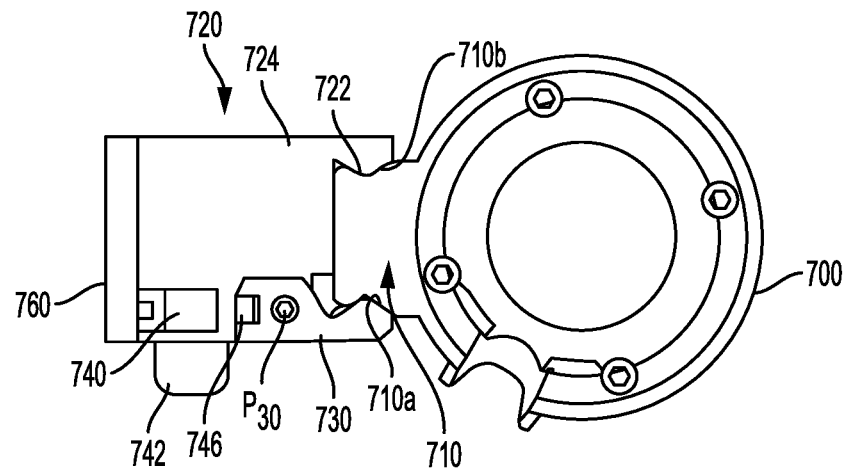
FIG. 7D is a top-down view of the trocar and the trocar support of FIG. 7A.
Figure 7E:
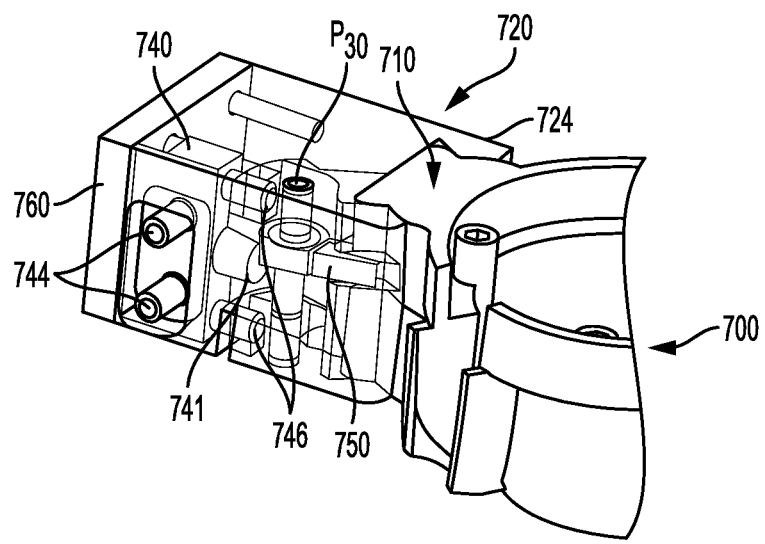
FIG. 7E is a partially transparent perspective view of the trocar and the trocar support of FIG. 7A.
Figure 7F:
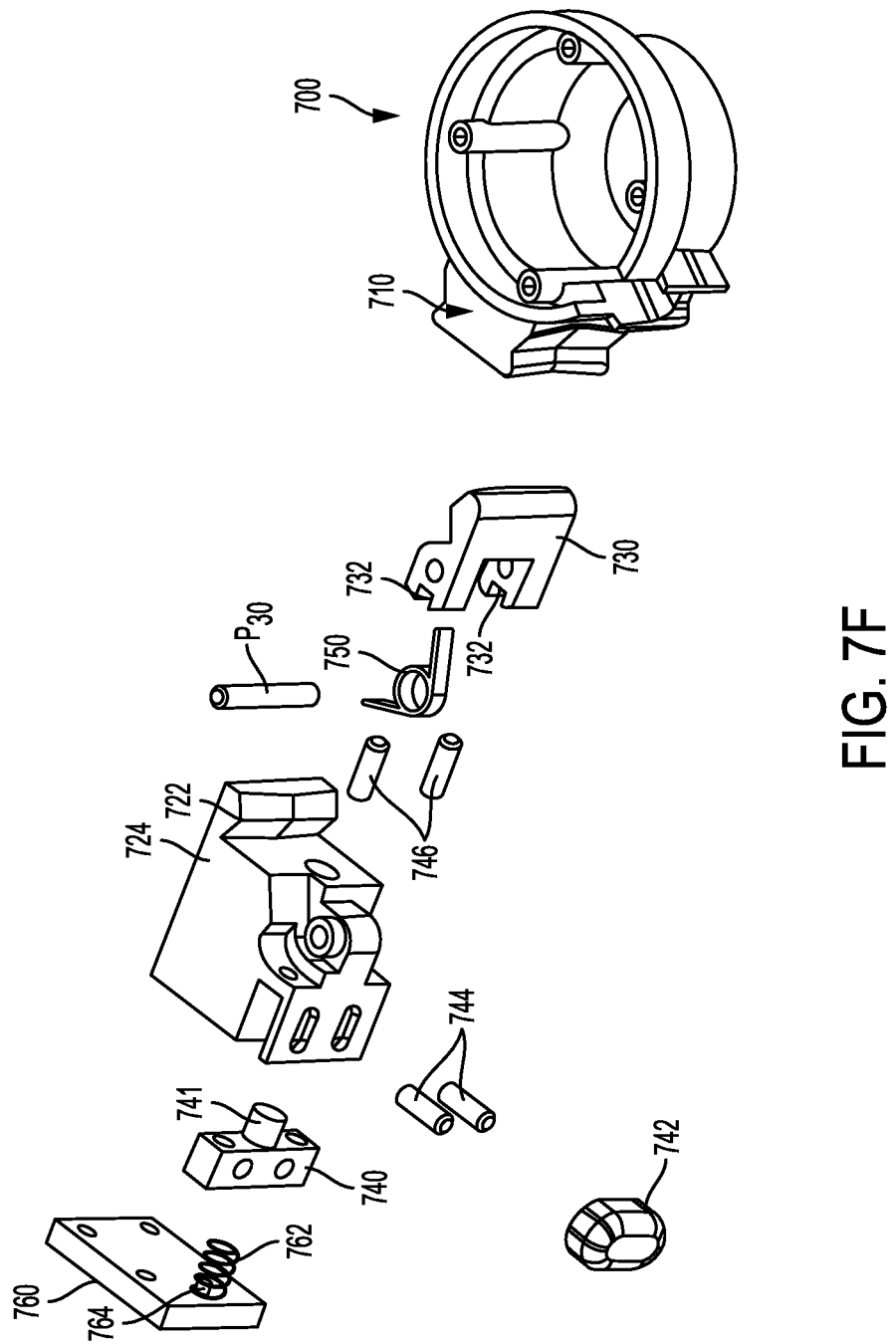
FIG. 7F is an exploded view of the trocar and the trocar support of FIG. 7A.

FIGS. 7A-7F illustrate another embodiment of a trocar 700 with a housing 702. A tool pathway extends therethrough with an opening 706 that is sized to receive an elongate shaft and an end effector of a surgical tool and a notch 705 formed in a sidewall thereof to receive insufflation tubing. A protrusion 708 extends proximally from the sidewall of the housing 702 and has opposing grooves 710a, 710b formed on opposite side surfaces thereof in a dovetail shape. The protrusion 710 is received into a cutout formed in a trocar support 720 with a housing 724. The trocar 700 can have additional engagement structures formed on a proximal side by the protrusion 710 that can also be received onto corresponding structures on the trocar support 720 to provide additional support and structural engagement between the trocar 700 and the trocar support 720. For example, proximal-most edges of the protrusion 710 can have dovetail shapes thereon, creating a double dovetail engagement. The grooves 710a, 710b are engaged by corresponding dovetail structures on the trocar support 720. Groove 710b engages a corresponding dovetail structure 722 on the trocar support, while groove 710a engages a hinged lever 730 with a corresponding dovetail structure. The hinged lever 730 is pivotably attached to the trocar support 720 by a pivot bar P30 and is biased to an open position by a torsion and/or compression spring 750. The hinged lever 730 also has two notches 732 on a proximal end thereof that receives a locking feature 734 therein. The locking feature 734 consists of a locking base 740 with an alignment protrusion 741, a knob 742, two support bars 744, and two locking bars 746. The support bars 744 pass through grooves in the support housing 724 and into the locking base 740. The locking base 740 is disposed in a recess of the housing 724 and is configured to move distally and proximally along a length of the grooves through which the support bars 744 pass. The knob 742 is disposed on an end of the support bars 744 externally to the housing 724 to act as a grip or handle to allow a user to slide the locking base 740. The two locking bars 746 extend distally from the locking base 740 and through holes formed in the housing 724 to allow distalmost ends of the locking bars 746 to contact the hinged lever 730. As the hinged lever 730 rotates, the locking bars 746 can engage and enter the notches 732 when the notches 732 align with the locking bars 746, locking the hinged lever 730 in place to prevent additional rotation and representing a locked or engaged position of the locking feature 734. A compression spring, for example spring 762, disposed on a support protrusion 764 on an attachment base 760 for assisting in attaching the trocar support 720 to a robotic arm as illustrated in FIG. 7E, can engage the locking base 740 and bias the locking base 740 distally so that, as the hinged lever 730 is rotated and the notches 732 align with the locking bars 746, the locking feature 734 can automatically lock the hinged lever 730.

When attaching the trocar 700 to the trocar support, the hinged lever 730 is biased to an opened position, as illustrated in FIGS. 7A and 7B, and the protrusion 710 is inserted into the cutout on the trocar support 720. When the groove 710b is engaged with the dovetail structure 722 on the trocar support 720, the hinged lever 730 is pivoted about the pivot bar P30 toward the protrusion 710 by overcoming the biasing force of the spring 750 until the hinged lever 730 engages with the groove 710a. If a compression spring is being used with the locking mechanism 734, then the locking bars 746 will automatically engage the notches 732 on the hinged lever 730. Otherwise the knob 742 can be manually slid distally to bring the locking bars 746 into engagement with the notches 732. At this point, the trocar 700 will be attached securely to the trocar support 720, as illustrated in FIGS. 7C-7E. To disengage the trocar 700, the knob 742 can be slid proximally, potentially overcoming the compression spring bias if one is being used, so that the locking bars 746 move proximally out of engagement with the notches 732. The rotating lever 730 will then pivot about the pivot bar P30 to an open position, being biased open by the spring 750. Magnets and/or additional supporting structures, lips, ledges, etc. can be incorporated into both distal surfaces of the trocar support 720 and proximal surfaces of the trocar 700 to act as guides, alignment, and stops as the trocar 700 is inserted into the trocar support 720.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
    a trocar having a housing and a cannula extending distally from the housing, the housing and the cannula defining a tool pathway extending therethrough for receiving a tool; and
    a trocar support configured to be mounted on a distal end of a surgical robotic arm, the trocar being configured to have a first position in which the trocar is coupled to the support being configured to engage the trocar in a first configuration that allows free rotation of the trocar around a longitudinal axis of the tool pathway relative to the trocar support, and in a second configuration in which the trocar is locked in a fixed position relative to the trocar support.

2. The system of claim 1, wherein the trocar support includes a latch configured to move the trocar support between the first and the second configurations.

3. The system of claim 2, wherein the latch is slidable to move the trocar support between the first configuration and the second configuration.

4. The system of claim 2, wherein the latch pivots to move the trocar support between the first configuration and the second configuration.

5. The system of claim 2, wherein the latch is biased to one of the first and second configurations.

6. The system of claim 1, wherein the trocar support includes a receiver having a shape that corresponds to a protrusion formed on the trocar for mating the trocar to the trocar support.

7. The system of claim 6, wherein the protrusion on the trocar entirely encircles and protrudes radially away from an outer surface of the trocar with respect to the longitudinal axis of the tool pathway.

8. The system of claim 1, wherein the trocar support includes a linkage assembly for mating the trocar to the trocar support in at least one of the first and second configurations.

9. The system of claim 1, wherein the trocar support in the first configuration is configured to prevent axial movement of the trocar along a longitudinal axis of the trocar.

10. The system of claim 1, further comprising a robotic arm having the trocar support mated thereto.

11. A surgical system, comprising:
a trocar having a housing and a cannula extending distally from the housing, the housing and the cannula defining a tool pathway extending therethrough for receiving a tool, the trocar having a mating element formed thereon; and
a trocar support configured to be mounted on a distal end of a surgical robotic arm and having at least one receiving feature thereon, the trocar being configured to freely mate to the trocar support to rotate around a longitudinal axis of the tool pathway when the mating element is seated within the receiving feature of the trocar support, and the trocar support having a lock configured to engage and prevent movement of the trocar relative to the trocar support.

12. The system of claim 11, further comprising alignment features on the trocar and the trocar support for aligning the trocar relative to the trocar support.

13. The system of claim 11, wherein the receiving feature is selected from the group consisting of a set of jaws, a sliding block, a hook, and a clamp.

14. A surgical system, comprising:
a trocar having a housing and a cannula extending distally from the housing, the housing and the cannula defining a tool pathway extending therethrough for receiving a tool, the trocar having a mating element formed thereon; and
a trocar support configured to be mounted on a distal end of a surgical robotic arm and having at least one receiving feature thereon, the trocar being configured to mate to the trocar support such that the receiving feature of the trocar support engages and prevents movement of the trocar relative to the trocar support, the receiving feature being configured to release the trocar to allow rotation of the trocar around a longitudinal axis of the tool pathway relative to the trocar support through a one-touch release mechanism.

15. A surgical method, comprising:
inserting a mating feature on a trocar into a receiving feature on a trocar support, the trocar having a housing and a cannula extending distally from the housing, the housing and the cannula defining a tool pathway extending therethrough for receiving a tool, the trocar being freely rotatable around a longitudinal axis of the tool pathway but not axially translatable relative to the trocar support; and
activating a locking element on the trocar support to prevent movement of the trocar relative to the trocar support.

16. The surgical method claim 15, further comprising, prior to activating the locking element, rotating the trocar around the longitudinal axis of the tool pathway such that the mating feature on the trocar rotatably slides within the receiving feature on the trocar support.

17. The surgical method claim 15, further comprising mating the trocar support to a robotic arm.

* * * * *